United States Patent
Ouyang et al.

(10) Patent No.: US 10,362,926 B2
(45) Date of Patent: *Jul. 30, 2019

(54) LOW-COST INSTRUMENT FOR ENDOSCOPICALLY GUIDED OPERATIVE PROCEDURES

(71) Applicant: CooperSurgical, Inc., Trumbull, CT (US)

(72) Inventors: Xiaolong Ouyang, Palo Alto, CA (US); Paul D. Indman, San Jose, CA (US); Robert K. Deckman, San Bruno, CA (US); Shih-Ping Wang, Los Altos, CA (US)

(73) Assignee: CooperSurgical, Inc., Trumbull, CT (US)

( * ) Notice: Subject to any disclaimer, the term of this patent is extended or adjusted under 35 U.S.C. 154(b) by 322 days.

This patent is subject to a terminal disclaimer.

(21) Appl. No.: 15/453,036

(22) Filed: Mar. 8, 2017

(65) Prior Publication Data

US 2017/0188794 A1 Jul. 6, 2017

Related U.S. Application Data

(63) Continuation of application No. 14/409,281, filed as application No. PCT/US2013/049074 on Jul. 2, 2013, (Continued)

(51) Int. Cl.
*A61B 1/00* (2006.01)
*A61B 1/303* (2006.01)
(Continued)

(52) U.S. Cl.
CPC ........ *A61B 1/00103* (2013.01); *A61B 1/0011* (2013.01); *A61B 1/00052* (2013.01);
(Continued)

(58) Field of Classification Search
CPC ..... A61B 1/00103; A61B 1/015; A61B 1/303; A61B 1/05; A61B 1/00128;
(Continued)

(56) References Cited

U.S. PATENT DOCUMENTS

| 4,137,920 A | 2/1979 | Bonnet |
| 4,201,199 A | 5/1980 | Smith |

(Continued)

FOREIGN PATENT DOCUMENTS

| CN | 2565407 | 8/2003 |
| CN | 2638669 | 9/2004 |

(Continued)

OTHER PUBLICATIONS

U.S. Appl. No. 12/911,297, filed Oct. 25, 2010, Ouyang.
(Continued)

*Primary Examiner* — Timothy J Neal
(74) *Attorney, Agent, or Firm* — Fish & Richardson P.C.

(57) ABSTRACT

Installments and methods are described for performing endoscopically guided operative procedures. According to some embodiments, a re-usable portion of the instrument includes a handle, electronics and an integrated display screen while a fluid hub and a cannula which includes a CMOS imaging module and LED lighting, form a single use portion of the instrument. The cannula includes a working channel configured to accept an operative device for performing the operative procedures.

12 Claims, 22 Drawing Sheets

Related U.S. Application Data now Pat. No. 9,622,646, which is a continuation-in-part of application No. PCT/US2013/040992, filed on May 14, 2013.

(60) Provisional application No. 61/818,341, filed on May 1, 2013, provisional application No. 61/813,635, filed on Apr. 18, 2013, provisional application No. 61/803,672, filed on Mar. 20, 2013, provisional application No. 61/803,664, filed on Mar. 20, 2013, provisional application No. 61/709,033, filed on Oct. 2, 2012, provisional application No. 61/709,022, filed on Oct. 2, 2012, provisional application No. 61/692,701, filed on Aug. 23, 2012, provisional application No. 61/676,444, filed on Jul. 27, 2012, provisional application No. 61/664,143, filed on Jun. 25, 2012, provisional application No. 61/672,733, filed on Jul. 17, 2012, provisional application No. 61/681,129, filed on Aug. 8, 2012, provisional application No. 61/667,341, filed on Jul. 2, 2012.

(51) Int. Cl.

| | | |
|---|---|---|
| *A61B 1/018* | (2006.01) | |
| *A61B 1/06* | (2006.01) | |
| *A61B 18/24* | (2006.01) | |
| *A61M 5/00* | (2006.01) | |
| *A61B 17/34* | (2006.01) | |
| *A61B 17/42* | (2006.01) | |
| *A61B 90/00* | (2016.01) | |
| *A61B 1/015* | (2006.01) | |
| *A61B 1/05* | (2006.01) | |
| *A61B 17/00* | (2006.01) | |
| *A61B 18/18* | (2006.01) | |

(52) U.S. Cl.
CPC ...... *A61B 1/00066* (2013.01); *A61B 1/00098* (2013.01); *A61B 1/00105* (2013.01); *A61B 1/00128* (2013.01); *A61B 1/00133* (2013.01); *A61B 1/015* (2013.01); *A61B 1/018* (2013.01); *A61B 1/05* (2013.01); *A61B 1/0676* (2013.01); *A61B 1/0684* (2013.01); *A61B 1/303* (2013.01); *A61B 17/00234* (2013.01); *A61B 17/3478* (2013.01); *A61B 17/42* (2013.01); *A61B 18/24* (2013.01); *A61B 90/361* (2016.02); *A61M 5/00* (2013.01); *A61B 2017/0034* (2013.01); *A61B 2017/0046* (2013.01); *A61B 2017/00115* (2013.01); *A61B 2017/00199* (2013.01); *A61B 2017/00738* (2013.01); *A61B 2017/4216* (2013.01); *A61B 2017/4233* (2013.01); *A61B 2018/1861* (2013.01); *A61B 2090/0807* (2016.02); *A61B 2217/005* (2013.01); *A61B 2217/007* (2013.01)

(58) Field of Classification Search
CPC .............. A61B 1/00066; A61B 1/0684; A61B 1/00052; A61B 1/00105; A61B 1/0676; A61B 1/018; A61B 17/3478; A61B 17/42; A61B 18/24; A61B 90/361; A61B 2017/00115; A61B 2017/00199; A61B 2017/0034; A61B 2017/0046; A61B 2017/4216; A61B 2017/4233; A61B 2018/1861

See application file for complete search history.

(56) References Cited

U.S. PATENT DOCUMENTS

| | | |
|---|---|---|
| 4,441,509 A | 4/1984 | Kotsifas et al. |
| 4,475,539 A | 10/1984 | Konomura |
| 4,836,189 A | 6/1989 | Alfred et al. |
| 4,867,138 A | 9/1989 | Kubota et al. |
| 5,483,951 A | 1/1996 | Frassica et al. |
| 5,484,422 A | 1/1996 | Sloane et al. |
| 5,498,230 A | 3/1996 | Adair |
| 5,506,912 A | 4/1996 | Nagasaki et al. |
| 5,527,262 A | 6/1996 | Monroe et al. |
| 5,591,119 A | 1/1997 | Adair |
| 5,609,561 A | 3/1997 | Uehara et al. |
| 5,637,074 A | 6/1997 | Andino et al. |
| 5,662,586 A | 9/1997 | Monroe et al. |
| 5,666,965 A | 9/1997 | Bales et al. |
| 5,734,418 A | 3/1998 | Danna |
| 5,751,341 A | 5/1998 | Chaleki et al. |
| 5,823,940 A | 10/1998 | Newman |
| 5,860,953 A | 1/1999 | Snoke et al. |
| 5,873,816 A | 2/1999 | Kagawa et al. |
| 5,879,289 A | 3/1999 | Yarush et al. |
| 5,885,214 A | 3/1999 | Monroe et al. |
| 5,902,230 A | 5/1999 | Takahashi et al. |
| 5,929,901 A | 7/1999 | Adair et al. |
| 5,986,693 A | 11/1999 | Adair et al. |
| 5,993,378 A | 11/1999 | Lemelson |
| 6,043,839 A | 3/2000 | Adair et al. |
| 6,066,089 A | 5/2000 | Costello et al. |
| 6,095,970 A | 8/2000 | Hidaka et al. |
| 6,102,920 A | 8/2000 | Sullivan et al. |
| 6,106,457 A | 8/2000 | Perkins et al. |
| 6,203,493 B1 | 3/2001 | Ben-Haim |
| 6,211,904 B1 | 4/2001 | Adair et al. |
| 6,221,007 B1 | 4/2001 | Green |
| 6,275,855 B1 | 8/2001 | Johnson |
| 6,310,642 B1 | 10/2001 | Adair et al. |
| 6,315,712 B1 | 11/2001 | Rovegno |
| 6,348,035 B1 | 2/2002 | Takami |
| 6,387,043 B1 | 5/2002 | Yoon |
| 6,419,626 B1 | 7/2002 | Yoon |
| 6,428,470 B1 | 8/2002 | Thompson |
| 6,468,265 B1 | 10/2002 | Evans et al. |
| 6,478,730 B1 | 11/2002 | Bala et al. |
| 6,554,765 B1 | 4/2003 | Yarushi et al. |
| 6,593,587 B2 | 7/2003 | Pease |
| 6,652,453 B2 | 11/2003 | Smith et al. |
| 6,709,408 B2 | 3/2004 | Fisher |
| 6,717,166 B2 | 4/2004 | Pease |
| 6,858,857 B2 | 2/2005 | Pease et al. |
| 6,858,858 B2 | 2/2005 | Pease |
| 6,923,757 B2 | 8/2005 | Abe et al. |
| 6,929,600 B2 | 8/2005 | Hill |
| 6,979,290 B2 | 12/2005 | Mourlas et al. |
| 6,982,740 B2 | 1/2006 | Adair et al. |
| 7,030,904 B2 | 4/2006 | Adair et al. |
| 7,033,314 B2 | 4/2006 | Kamrava et al. |
| 7,041,050 B1 | 5/2006 | Ronald |
| 7,074,182 B2 | 7/2006 | Rovegno |
| 7,081,097 B2 | 7/2006 | Martone et al. |
| 7,099,078 B2 | 8/2006 | Spencer |
| 7,144,250 B2 | 12/2006 | Fischer et al. |
| 7,214,183 B2 | 5/2007 | Miyake |
| 7,365,768 B1 | 4/2008 | Ono et al. |
| 7,384,308 B2 | 6/2008 | Boehnlein et al. |
| 7,431,619 B2 | 10/2008 | Boehnlein et al. |
| 7,445,596 B2 | 11/2008 | Kucklick et al. |
| 7,500,947 B2 | 3/2009 | Kucklick et al. |
| 7,520,854 B2 | 4/2009 | Sato |
| 7,530,946 B2 | 5/2009 | Hartwick |
| 7,581,988 B2 | 9/2009 | Boehnlein et al. |
| 7,584,534 B2 | 9/2009 | Pease et al. |
| 7,758,495 B2 | 7/2010 | Pease et al. |
| 7,783,133 B2 | 8/2010 | Dunki-Jacobs et al. |
| 7,794,409 B2 | 9/2010 | Damarati |
| 7,846,107 B2 | 12/2010 | Hoffman et al. |
| 7,850,601 B2 | 12/2010 | Uchimura et al. |

(56) References Cited

U.S. PATENT DOCUMENTS

| | | |
|---|---|---|
| 7,927,272 B2 | 4/2011 | Bayer et al. |
| 7,946,981 B1 | 5/2011 | Cubb |
| 7,959,561 B2 | 6/2011 | Akui et al. |
| 7,976,459 B2 | 7/2011 | Laser |
| 7,979,689 B2 | 7/2011 | Watt et al. |
| 8,004,560 B2 | 8/2011 | Sato et al. |
| 8,007,433 B2 | 8/2011 | Iketani |
| 8,022,979 B2 | 9/2011 | Miyamoto et al. |
| 8,025,670 B2 | 9/2011 | Sharp et al. |
| 8,033,993 B2 | 10/2011 | Amano et al. |
| 8,133,169 B2 | 3/2012 | Nagase et al. |
| 8,142,346 B2 | 3/2012 | Shoroji et al. |
| 8,144,191 B2 | 3/2012 | Kawanishi et al. |
| 8,157,726 B2 | 4/2012 | Melder |
| 8,177,710 B1 | 5/2012 | Hosaka et al. |
| 8,182,416 B1 | 5/2012 | Hosaka et al. |
| 8,189,043 B2 | 5/2012 | Schneider et al. |
| 8,218,074 B2 | 7/2012 | Pease et al. |
| 8,317,689 B1 | 11/2012 | Remijan et al. |
| 8,356,527 B2 | 1/2013 | Hudson |
| 8,382,665 B1 | 2/2013 | Fam |
| 8,403,831 B2 | 3/2013 | Kishioka |
| 8,416,291 B2 | 4/2013 | Carrey et al. |
| 8,453,639 B2 | 6/2013 | Kim et al. |
| 8,460,182 B2 | 6/2013 | Ouyang et al. |
| 8,535,219 B2 | 9/2013 | Smith et al. |
| 8,556,801 B2 | 10/2013 | Liu |
| 8,574,151 B2 | 11/2013 | Mitsuhashi |
| 8,581,971 B2 | 11/2013 | Miyamoto et al. |
| 8,591,401 B2 | 11/2013 | Miyayashiki et al. |
| 8,597,179 B2 | 12/2013 | Kokubo |
| 8,638,361 B2 | 1/2014 | Tanabe et al. |
| 8,641,605 B2 | 2/2014 | Shoroji et al. |
| 8,656,697 B2 | 2/2014 | Zubiate et al. |
| 8,872,906 B2 | 10/2014 | Bayer et al. |
| 9,622,646 B2 * | 4/2017 | Ouyang .............. A61B 1/00103 |
| 2002/0077550 A1 | 6/2002 | Rabiner et al. |
| 2003/0040659 A1 | 2/2003 | Kazakevish |
| 2003/0195390 A1 | 10/2003 | Graumann |
| 2004/0054254 A1 | 3/2004 | Miyake |
| 2004/0122327 A1 | 6/2004 | Belson et al. |
| 2004/0210161 A1 | 10/2004 | Burdorff et al. |
| 2004/0220478 A1 | 11/2004 | Wallace et al. |
| 2005/0010081 A1 | 1/2005 | Dogushi et al. |
| 2005/0075538 A1 | 4/2005 | Banik et al. |
| 2005/0085690 A1 | 4/2005 | Tien |
| 2005/0136372 A1 | 6/2005 | Fischer et al. |
| 2006/0004258 A1 | 1/2006 | Sun et al. |
| 2006/0058703 A1 | 3/2006 | Huenerbein |
| 2006/0103729 A1 | 5/2006 | Burns et al. |
| 2006/0106281 A1 | 5/2006 | Boulais et al. |
| 2006/0155168 A1 | 7/2006 | Pease |
| 2006/0184187 A1 | 8/2006 | Surti |
| 2006/0258955 A1 | 11/2006 | Hoffman et al. |
| 2007/0030344 A1 | 2/2007 | Miyamoto et al. |
| 2007/0033626 A1 | 2/2007 | Yang et al. |
| 2007/0038020 A1 | 2/2007 | Tien |
| 2007/0129604 A1 | 6/2007 | Hatcher et al. |
| 2007/0167681 A1 | 7/2007 | Gill et al. |
| 2007/0185379 A1 | 8/2007 | Newman et al. |
| 2007/0225556 A1 | 9/2007 | Ortiz et al. |
| 2007/0225561 A1 | 9/2007 | Watanabe et al. |
| 2007/0249904 A1 | 10/2007 | Amano et al. |
| 2007/0265492 A1 | 11/2007 | Sonnenschein et al. |
| 2008/0042861 A1 | 2/2008 | Dacquay et al. |
| 2008/0045791 A1 | 2/2008 | Gal et al. |
| 2008/0046293 A1 | 2/2008 | Yamada et al. |
| 2008/0051628 A1 | 2/2008 | Pecherer et al. |
| 2008/0058591 A1 | 3/2008 | Saadat et al. |
| 2008/0058595 A1 | 3/2008 | Snoke et al. |
| 2008/0076966 A1 | 3/2008 | Isaacson |
| 2008/0086028 A1 | 4/2008 | Matsui |
| 2008/0097469 A1 | 4/2008 | Gruber et al. |
| 2008/0097470 A1 | 4/2008 | Gruber et al. |
| 2008/0108869 A1 | 5/2008 | Sanders et al. |
| 2008/0132763 A1 | 6/2008 | Isaacson |
| 2008/0195128 A1 | 8/2008 | Orbay et al. |
| 2008/0200758 A1 | 8/2008 | Orbay et al. |
| 2008/0243031 A1 | 10/2008 | Seibel et al. |
| 2009/0026888 A1 | 1/2009 | Melville |
| 2009/0030276 A1 | 1/2009 | Saadat et al. |
| 2009/0036742 A1 | 2/2009 | Watanabe |
| 2009/0082695 A1 | 3/2009 | Whitehead |
| 2009/0105538 A1 | 4/2009 | Van Dam et al. |
| 2009/0112058 A1 | 4/2009 | Kagawa |
| 2009/0118575 A1 | 5/2009 | Ichikawa et al. |
| 2009/0118580 A1 | 5/2009 | Sun et al. |
| 2009/0167849 A1 | 7/2009 | Niida |
| 2009/0196459 A1 | 8/2009 | Watt et al. |
| 2009/0221873 A1 | 9/2009 | McGrath |
| 2009/0225159 A1 | 9/2009 | Schneider et al. |
| 2009/0231419 A1 | 9/2009 | Bayer |
| 2009/0312607 A1 | 12/2009 | Sunagawa et al. |
| 2009/0318758 A1 | 12/2009 | Farr et al. |
| 2010/0022824 A1 | 1/2010 | Cybulski |
| 2010/0030020 A1 | 2/2010 | Sanders et al. |
| 2010/0033563 A1 | 2/2010 | Boehnlein et al. |
| 2010/0033986 A1 | 2/2010 | Schober et al. |
| 2010/0095969 A1 | 4/2010 | Schwartz et al. |
| 2010/0121139 A1 | 5/2010 | Ouyang et al. |
| 2010/0121142 A1 | 5/2010 | Ouyang et al. |
| 2010/0121155 A1 | 5/2010 | Ouyang et al. |
| 2010/0125164 A1 | 5/2010 | LaBombard |
| 2010/0128116 A1 | 5/2010 | Sato et al. |
| 2010/0185052 A1 | 7/2010 | Chang |
| 2010/0191050 A1 | 7/2010 | Zwolinski |
| 2010/0238278 A1 | 9/2010 | Rovegno |
| 2010/0262000 A1 | 10/2010 | Wallace et al. |
| 2010/0284580 A1 | 11/2010 | Ouyang et al. |
| 2010/0286477 A1 | 11/2010 | Ouyang et al. |
| 2011/0009694 A1 | 1/2011 | Schultz et al. |
| 2011/0034773 A1 | 2/2011 | Ishigami et al. |
| 2011/0090331 A1 | 4/2011 | Draper |
| 2011/0092842 A1 | 4/2011 | Decaria et al. |
| 2011/0112360 A1 | 5/2011 | Swann et al. |
| 2011/0112361 A1 | 5/2011 | Ishigami et al. |
| 2011/0130627 A1 | 6/2011 | McGrail et al. |
| 2011/0130632 A1 | 6/2011 | McGrail et al. |
| 2011/0137127 A1 | 6/2011 | Schwartz et al. |
| 2011/0152878 A1 | 6/2011 | Trusty et al. |
| 2011/0160537 A1 | 6/2011 | Chen |
| 2011/0187824 A1 | 8/2011 | Hori |
| 2011/0201884 A1 | 8/2011 | Kishioka |
| 2011/0218457 A1 | 9/2011 | Song et al. |
| 2011/0270038 A1 | 11/2011 | Jiang et al. |
| 2011/0270179 A1 | 11/2011 | Ouyang et al. |
| 2011/0273556 A1 | 11/2011 | Lyons et al. |
| 2011/0276113 A1 | 11/2011 | Cybulski |
| 2012/0095458 A1 | 4/2012 | Cybulski |
| 2012/0099735 A1 | 4/2012 | Chen |
| 2012/0100729 A1 | 4/2012 | Ouyang et al. |
| 2012/0109007 A1 | 5/2012 | Rhad et al. |
| 2012/0116160 A1 | 5/2012 | Nieman et al. |
| 2012/0130160 A1 | 5/2012 | Borrye |
| 2012/0209065 A1 | 8/2012 | Hosaka et al. |
| 2012/0209066 A1 | 8/2012 | Hosaka et al. |
| 2012/0209067 A1 | 8/2012 | Hosaka et al. |
| 2012/0265009 A1 | 10/2012 | Ouyang et al. |
| 2012/0277528 A1 | 11/2012 | Qiao |
| 2012/0289778 A1 | 11/2012 | Chan |
| 2012/0307039 A1 | 12/2012 | Holmes |
| 2012/0310045 A1 | 12/2012 | Hu et al. |
| 2012/0323073 A1 | 12/2012 | Azuma et al. |
| 2013/0041220 A1 | 2/2013 | Kutsuma |
| 2013/0046316 A1 | 2/2013 | Sullivan et al. |
| 2013/0050455 A1 | 2/2013 | Yagi |
| 2013/0066151 A1 | 3/2013 | Chen |
| 2013/0066152 A1 | 3/2013 | Chen |
| 2013/0072754 A1 | 3/2013 | Okamoto et al. |
| 2013/0079594 A1 | 3/2013 | Motoki |
| 2013/0096376 A1 | 4/2013 | Takei et al. |
| 2013/0225924 A1 | 8/2013 | Simms et al. |
| 2013/0231533 A1 | 9/2013 | Papademetriou et al. |
| 2013/0244453 A1 | 9/2013 | Sakamoto |

(56) References Cited

U.S. PATENT DOCUMENTS

| | | |
|---|---|---|
| 2013/0253368 A1 | 9/2013 | Are et al. |
| 2013/0289347 A1 | 10/2013 | Ito et al. |
| 2013/0296648 A1 | 11/2013 | Ouyang et al. |
| 2013/0303846 A1 | 11/2013 | Cybulski |
| 2013/0345503 A1 | 12/2013 | Friedrich |
| 2013/0345518 A1 | 12/2013 | Law et al. |
| 2014/0031621 A1 | 1/2014 | Liu |
| 2014/0039253 A1 | 2/2014 | Fang et al. |
| 2014/0073853 A1 | 3/2014 | Swisher et al. |
| 2014/0276207 A1 | 9/2014 | Ouyang et al. |
| 2014/0288460 A1 | 9/2014 | Ouyang et al. |
| 2016/0174819 A1 | 6/2016 | Ouyang et al. |

FOREIGN PATENT DOCUMENTS

| | | | |
|---|---|---|---|
| CN | 2754555 | 2/2006 | |
| CN | 1924779 | 3/2007 | |
| CN | 101422351 | 5/2009 | |
| CN | 201282962 | 8/2009 | |
| CN | 201641951 | 11/2010 | |
| CN | 201658404 | 12/2010 | |
| CN | 201701193 | 1/2011 | |
| JP | 10-155736 | 6/1998 | ............... A61B 1/04 |
| JP | 10-508240 | 8/1998 | |
| JP | 2003-88499 | 3/2003 | |
| JP | 2007-252559 | 10/2007 | |
| JP | 2010-506669 | 3/2010 | |
| WO | WO 1994/008512 | 4/1994 | |
| WO | WO 2001/029817 | 4/2001 | |
| WO | WO 2001/219817 | 10/2001 | |
| WO | WO 2008/048688 | 4/2008 | |
| WO | WO 2009/150231 | 12/2009 | |
| WO | WO 2010/011781 | 1/2010 | |
| WO | WO 2011/006052 | 1/2011 | |
| WO | WO 2011/038310 | 3/2011 | |
| WO | WO 2012/060932 | 5/2012 | |
| WO | WO 2012/151073 | 11/2012 | |

OTHER PUBLICATIONS

International Search Report for International Application No. PCT/US13/40992, dated Oct. 17, 2013 (3 pages).

International Search Report for International Application No. PCT/US13/49074, dated Oct. 1, 2013 (1 page).

EndoSee Corporation Brochure, www.endosee.com, Apr. 2013, 2 pages.

Ethicon Versascope Brochure VS001R2, S/06, 6 pages.

U.S. Appl. No. 12/911,297 entitled "Integrated Hysteroscopy and Endometrial Sampling Device" filed Oct. 25, 2010.

* cited by examiner

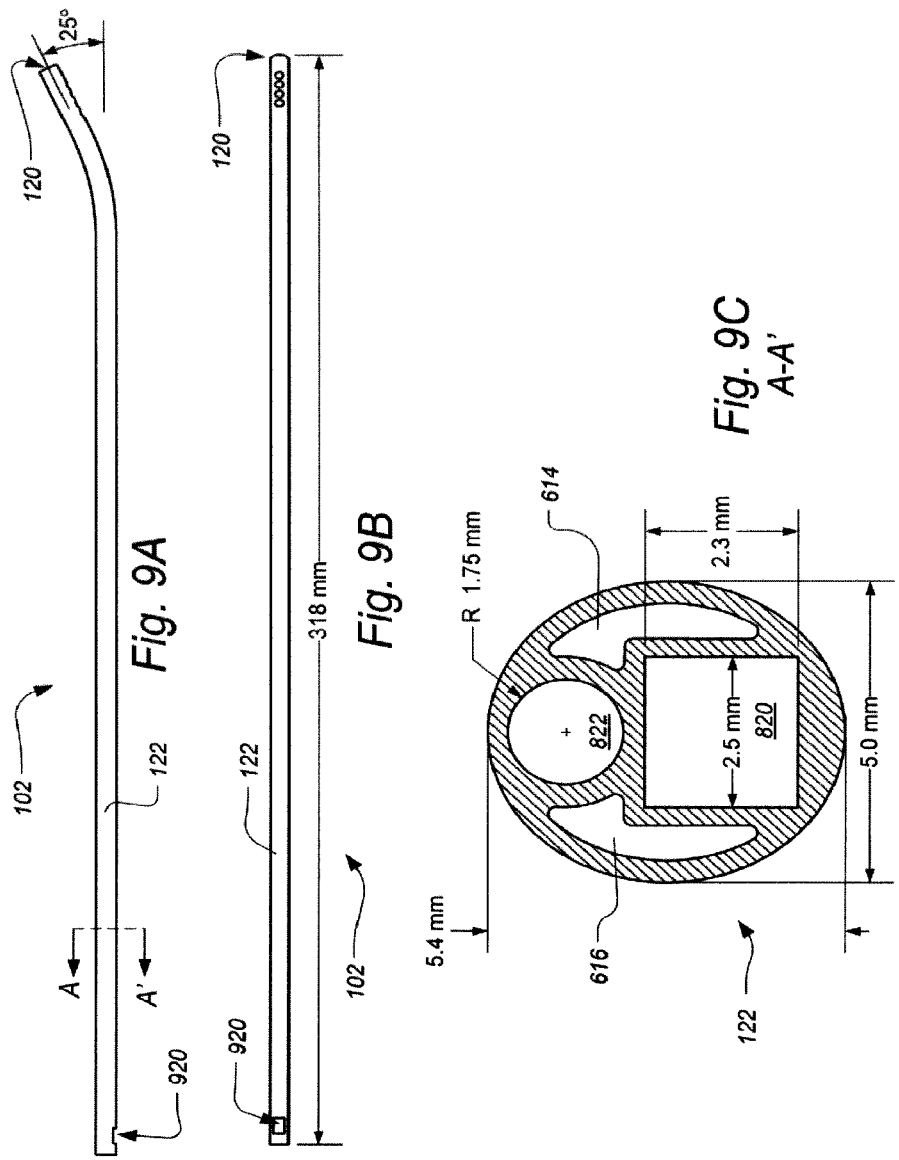

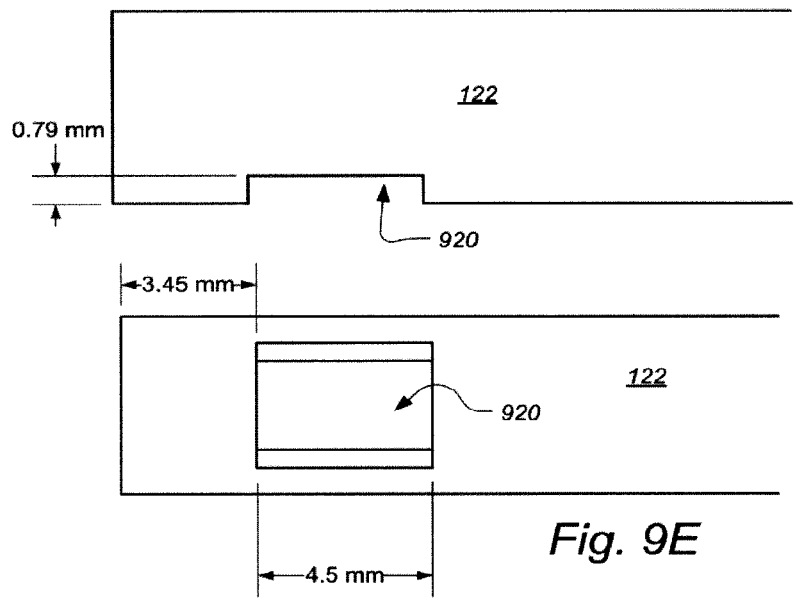
Fig. 9D
Fig. 9E
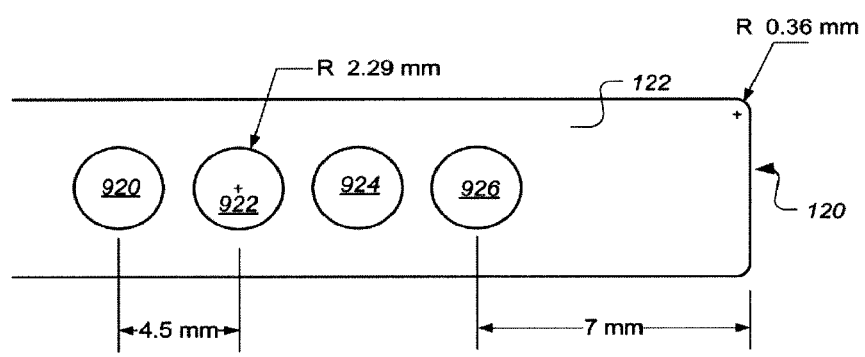
Fig. 9F

LOW-COST INSTRUMENT FOR ENDOSCOPICALLY GUIDED OPERATIVE PROCEDURES

REFERENCE TO RELATED APPLICATIONS

This patent application is a continuation of U.S. application Ser. No. 14/409,281, filed on Dec. 18, 2014, which is a 371 U.S. National Application of PCT/US2013/049074, dated Jul. 2, 2013, which is a continuation in part of U.S. National Application No. PCT/US2013/40992 dated May 14, 2014, and claims the priority benefit of and incorporates by reference each of the following applications:

U.S. Prov. Ser. No. 61/667,341 filed Jul. 2, 2012;
U.S. Prov. Ser. No. 61/664,143 filed Jun. 25, 2012;
U.S. Prov. Ser. No. 61/672,733 filed Jul. 17, 2012;
U.S. Prov. Ser. No. 61/676,444 filed Jul. 27, 2012;
U.S. Prov. Ser. No. 61/681,129 filed Aug. 8, 2012;
U.S. Prov. Ser. No. 61/692,701 filed Aug. 23, 2012;
U.S. Prov. Ser. No. 61/709,022 filed Oct. 2, 2012;
U.S. Prov. Ser. No. 61/709,033 filed Oct. 2, 2012;
U.S. Prov. Ser. No. 61/803,664 filed Mar. 20, 2013;
U.S. Prov. Ser. No. 61/803,672 filed Mar. 20, 2013;
U.S. Prov. Ser. No. 61/813,635 filed Apr. 18, 2013; and
U.S. Prov. Ser. No. 61/818,341 filed May 1, 2013

The subject matter of this patent specification relates to the subject matter of the following applications, each of which is incorporated by reference herein:

U.S. Ser. No. 12/911,297 filed Oct. 25, 2010;
U.S. Prov. Ser. No. 61/415,771 filed Nov. 19, 2010;
U.S. Prov. Ser. No. 61/418,248, filed Nov. 30, 2010;
U.S. Prov. Ser. No. 61/429,093 filed Dec. 31, 2010;
U.S. Prov. Ser. No. 61/431,316 filed Jan. 10, 2011;
U.S. Prov. Ser. No. 61/437,687, filed Jan. 30, 2011;
U.S. Prov. Ser. No. 61/444,098, filed Feb. 17, 2011;
U.S. Prov. Ser. No. 61/450,115, filed Mar. 7, 2011;
U.S. Prov. Ser. No. 61/453,533, filed Mar. 16, 2011;
U.S. Prov. Ser. No. 61/476,754, filed Apr. 18, 2011;
U.S. Prov. Ser. No. 61/482,200, filed May 3, 2011;
U.S. Prov. Ser. No. 61/482,309, filed May 4, 2011;
U.S. Prov. Ser. No. 61/485,601 filed May 12, 2011;
U.S. Prov. Ser. No. 61/490,029 filed May 25, 2011;
U.S. Prov. Ser. No. 61/494,400 filed Jun. 7, 2011;
U.S. Prov. Ser. No. 61/506,074 filed Jul. 9, 2011;
U.S. Prov. Ser. No. 61/515,092 filed Aug. 4, 2011;
U.S. Prov. Ser. No. 61/539,736 filed Sep. 27, 2011;
U.S. Prov. Ser. No. 61/544,280 filed Oct. 7, 2011;
U.S. Prov. Ser. No. 61/550,391 filed Oct. 22, 2011;
U.S. Prov. Ser. No. 61/555,470 filed Nov. 3, 2011;
U.S. Prov. Ser. No. 81/556,167 filed Nov. 4, 2011;
International Patent Appl. No. PCT/US11/51982 filed Sep. 16, 2011;
U.S. Prov. Ser. No. 61/539,736 filed Sep. 27, 2011;
U.S. Prov. Ser. No. 61/544,280 filed Oct. 7, 2011;
U.S. Prov. Ser. No. 61/550,391 filed Oct. 22, 2011;
U.S. Prov. Ser. No. 61/555,470 filed Nov. 3, 2011;
U.S. Prov. Ser. No. 61/556,167 filed Nov. 4, 2011;
U.S. Prov. Ser. No. 61/570,816 filed Dec. 14, 2011;
U.S. Prov. Ser. No. 61/599,981 filed Feb. 17, 2012;
U.S. Prov. Ser. No. 61/600,593 filed Feb. 18, 2012;
U.S. Prov. Ser. No. 61/611,182 filed Mar. 15, 2012;
U.S. Prov. Ser. No. 61/623,376 filed Apr. 12, 2012;
International Patent Appl. No. PCT/US2012/34698 filed Apr. 23, 2012;
U.S. Prov. Ser. No. 61/646,887 filed May 14, 2012; and
International Patent Appl. No. PCT/US2013/40992 filed May 14, 2013.

The above-referenced provisional and non-provisional patent applications are collectively referenced herein as "the commonly assigned incorporated applications."

FIELD

The present patent specification generally relates mainly to an endoscopic medical device having a working channel for operative procedures. More particularly, some embodiments relate to a self-contained, low-cost medical instrument for examining and performing operative procedures on a patient's uterus and/or uterine tubes, where the instrument has a single-use portion and a multiple-use portion.

BACKGROUND

Hysteroscopy, or direct vision of the inside of the uterus (referred to herein as the "uterine cavity" and/or "endometrial cavity"), has been shown to greatly improve diagnostic accuracy. Few gynecologists do office hysteroscopy, however, because of the complexity and expense of the equipment and supplies required. Conventional endoscopes are typically tethered and cumbersome to use. They require skilled staff to operate and maintain. This makes it especially difficult in time critical locations such as an emergency room, operating room, and other areas of a medical facility where multiple devices and instruments are being used simultaneously.

Furthermore, conventional endoscopes are relatively expensive and need to be sterilized after each use. Therefore, some medical facilities choose to stock multiple expensive devices so that when one device is being sterilized, which can be quite time-consuming, another device can be ready for use. Other facilities, such as an office may decide to own only one conventional endoscope due to cost considerations, but has to deal with the device not being available when it is being sterilized.

There are many indications for operative hysteroscopy which can frequently be done in an office setting if instrumentation is available. Such procedures include the tubal sterilization using a catheter passed through the operative channel of a hysteroscope, removal of polyps and other intrauterine pathology using hysteroscopic scissors, forceps, and biopsy devices introduced through the operative channel of a hysteroscope, treatment of submucous fibroids with electrosurgical instruments introduced through the operative channel of a hysteroscope, and lysis of intrauterine adhesions (cutting scar tissue) with hysteroscopic scissors introduced through the operative channel of a hysteroscope. Only a small percentage of gynecologists offer these treatments in an office setting because of the expense of setting up a conventional hysteroscopy system and the time and labor required to set up and maintain it.

The subject matter claimed herein is not limited to embodiments that solve any specific disadvantages or that operate only in environments such as those described above. Rather, this background is only provided to illustrate one exemplary technology area where some embodiments described herein may be practiced.

SUMMARY

According to some embodiments, a low-cost hand-held medical instrument is described for performing an endoscopically-guided operative procedure on a patient's uterus. The instrument includes a single-use portion that comprises: an elongated conduit having a distal portion configured and dimensioned for insertion into the patient's uterus through the patient's cervix, and a proximal portion; one or more fluid connection ports formed at the proximal portion of the conduit; one or more distal openings at the distal portion of the conduit configured to provide fluid from the conduit and into the uterus; an imaging system at the distal portion of the conduit configured to image the uterus and provide video signals; an Illumination system at the distal portion of the conduit configured to illuminate the uterus at an illumination field viewed by the imaging system; an electrical cable extending from a proximal end of the conduit to the imaging system and configured to carry video signals and control signals; and a working channel within the conduit including an entry point at the proximal portion and a distal opening at the distal portion, the working channel configured to allow passage of an operative device configured to perform the operative procedure inserted at the entry point. The instrument also includes a multiple-use portion having interior and exterior surfaces, the multiple-use portion being configured to be attached to the single-use portion for a single use and then detached after a single use, and to be re-used with a second single-use portion without sterilization of the interior surfaces, the multiple-use portion comprising an integral image display that is electrically coupled with the imaging system at least in part by the electrical cable, the display being configured to display images provided by the imaging system for viewing by a user. One or more seals are configured to prevent fluid in the conduit from contacting the interior surfaces of the multiple-use portion.

According to some embodiments, the instrument is configured for the operative procedure such that in when the distal portion is inserted into the patient's uterus to simultaneously provide (a) imaging portions of the uterus by illuminating portions of the uterus with the illumination system, imaging the illuminated portions of the uterus with the imaging system, and delivering fluid flow in a distal direction by introducing fluid under positive pressure into a first fluid connection port, which fluid passes through the a fluid channel and enters the uterus through at least a first distal opening, and (b) displaying live video images from the imaging system to an operator on the integral image display of the imaged portions of the uterus, the live video images aiding the operator in performing the operative procedure.

According to some embodiments, one or more of the seals are formed by an ultrasonic bonding process during manufacture. According to some embodiments, the proximal portion of the conduit includes an outer shell fabricated as two pieces that are bonded together using an ultrasonic bonding process during manufacture.

According to some embodiments, the operative procedure is a tubal sterilization procedure, and the distal portion of the conduit is bent at an angle of between 15 degrees and 35 degrees from the central longitudinal axis of the conduit.

According to some other embodiments, the operative procedure is localized drug delivery, and the operative device includes an injection needle. The proximal portion of the conduit can include an alignment guide member to aid in insertion of the injection needle through the entry point of the working channel. The injection needle can also include one or more markings on the exterior of the needle configured to visually aid an operator in controlling a depth of deployment of the injection needle. The distal portion of the injection needle can include a beveled portion shaped so as to facilitate passage of the injection needle through the working channel. The working channel can includes a valve and/or a non-wetting surface material so as to inhibit backflow of fluid from the patient through the working channel and out of the working channel entry point.

According to some embodiments, a method is described for performing an operative procedure in a patient's uterus with a hand-held, self-contained instrument. The method includes: releasably attaching by hand a sterile single-use portion of the instrument to a multiple-use portion of the instrument; introducing a distal portion of a single-use portion of the instrument into the patients uterus, the single-use portion comprising an elongated conduit including a working channel having an operative device entry point at a proximal portion of the conduit and an operative device distal opening at the distal portion, the conduit further including one or more internal fluid channels in fluid communication with one or more distal openings at the distal portion of the instrument; illuminating a portion of the patient's uterus with an illumination system emitting light at the distal end of the instrument; imaging the uterus while illuminated with an imaging system located at the distal end of the instrument; sending live video format images of the uterus from the imaging system through a cable in the conduit; displaying the live video images on a display that is a part of the multiple-use portion of the instrument and is connected to the cable; performing the operative procedure under guidance of the displayed live video images using an operative device disposed within the working channel of the conduit; keeping fluid from the conduit from contaminating interior portions of the multiple-use portion through the use of one or more fluid barriers in the instrument; releasing by hand and removing the single-use portion from the multiple-use portions; and attaching a new sterile single-use portion to the multiple-use portions to prepare the instrument for performing another operative procedure.

BRIEF DESCRIPTION OF THE DRAWINGS

To further clarify the above and other advantages and features of the subject matter of this patent specification, specific examples of embodiments thereof are illustrated in the appended drawings. It should be appreciated that these drawings depict only illustrative embodiments and are therefore not to be considered limiting of the scope of this patent specification or the appended claims. The subject matter hereof will be described and explained with additional specificity and detail through the use of the accompanying drawings in which:

FIGS. 9A-F illustrate various aspects of a cannula for a self-contained, low-cost medical instrument for examining and performing operative procedures, according to some embodiments;

DETAILED DESCRIPTION

A detailed description of examples of preferred embodiments is provided below. While several embodiments are described, it should be understood that the new subject matter described in this patent specification is not limited to any one embodiment or combination of embodiments described herein, but instead encompasses numerous alternatives, modifications, and equivalents. In addition, while numerous specific details are set forth in the following description in order to provide a thorough understanding work, some embodiments can be practiced without some or all of these details. Moreover, for the purpose of clarity, certain technical material that is known in the related art has not been described in detail in order to avoid unnecessarily obscuring the new subject matter described herein. It should be clear that individual features of one or several of the specific embodiments described herein can be used in combination with features or other described embodiments. Further, like reference numbers and designations in the various drawings indicate like elements.

Figure 1:
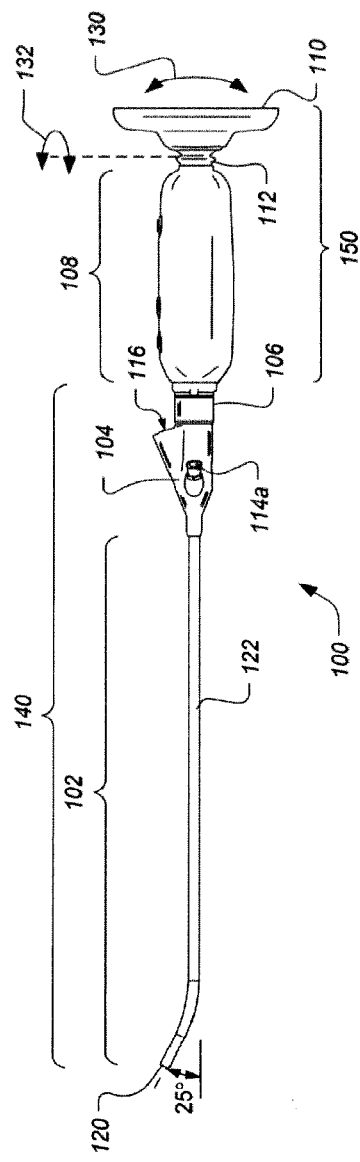
FIG. 1 is a left side view of a self-contained, low-cost medical instrument for examining and performing operative procedures, according to some embodiments.

FIG. 1 is a left side view of a self-contained, low-cost medical instrument for examining and performing operative procedures, according to some embodiments. Many of the elements of the embodiments of hysteroscope 100 shown in FIG. 1 are the same as or similar to those discussed in the embodiments described in the commonly assigned incorporated applications, and such elements may not be described or may only briefly be described. It will also be appreciated that the aspects of the embodiments described in the commonly assigned incorporated applications may also apply to the embodiments described herein.

The device 100 is particularly advantageous for enabling a physician to perform endoscopically-guided operative procedures in an efficient and cost-effective manner, although it is to be appreciated that other uses for hysteroscope 100 are within the scope of the present teachings. For example, as will be described in further detail, infra, the device 100 can be fitted with other types of cannulas that are configured for other types of procedures such as hysteroscopy with or without biopsy. The hysteroscope device 100 can bring about substantial efficiencies in terms of keeping equipment costs low and keeping the time required to perform the procedure modest. Hysteroscope 100 includes a operative cannula 102, fluid hub 104, sliding connector 106, handle body 108, display mount 112 and display 110. The operative cannula 102 is made of a distal tip 120 and a shaft 122. The fluid hub in this case includes two fluid ports 114a and 114b (shown in FIG. 2). In the example shown in FIG. 1, fluid port 114a is configured to deliver fluid Into the device and thus into the uterus, and fluid port 114b is configured to apply suction to extract fluid and/or tissue samples from the uterus. As shown, the shaft 122 is curved near its distal end, for example having a 25 degree bend as shown. The bend of shaft 122 near its distal end can be of an amount according to the anticipated operative procedure (s). For example, it has been found that a bend of 25 degrees is suitable for applications such as tubal sterilization since that bending amount aids in aligning the distal end of the cannula 102 with fallopian tubes (i.e. the distal end is co-axial (or co-linear) with the fallopian tube). For other operative procedures, such as anesthesia delivery to the fundus using an injection needle a straight or non-bent cannula may be suitable. According to some embodiments the bending amount of the distal end of the cannula 120 also aids in providing a wider field of visualization by twisting or rotating the device to different angles while in use. According to some embodiments, a bend of between 15 and 35 degrees near the distal end has been found to be suitable for many applications. The distal tip 120 includes a video camera assembly, lighting elements and fluid ports for in-flow (i.e. out of the device 100 and into the patient) and out-flow (i.e. into the device 100 and out of the patient). Operative cannula 102 further includes an operative channel accessible through operative device entry point 116. The operative channel can be used with an operative device such as an catheter used for tubal sterilization (e.g. Essure® transcervical sterilization catheter available from Conceptus Inc., which is depicted in many embodiments described herein). Other examples of operative procedures that can be used with operative cannula 102 include: removal of polyps and other intrauterine pathology using hysteroscopic scissors, forceps, and biopsy devices introduced through the operative channel of a hysteroscope, treatment of submucous fibroids with electrosurgical instruments introduced through the operative channel of a hysteroscope, and lysis of intrauterine adhesions (cutting scar tissue) with hysteroscopic scissors introduced through the operative channel of the hysteroscope 100. According to some embodiments, the operative channel of cannula 102 can be used with any of a number of different operative devices including but not limited to: needles (e.g. for injection and/or aspiration; forceps (e.g. for biopsy and/or grasping); surgical scissors; clip fixing/ligating devices; electrosurgical electrodes, fibers or cables for delivery of microwave, laser, and/or other energy sources; knives; catheters, cleaning devices; and balloon dilators.

According to some embodiments, the outer shell of tip 120 and shaft 122 are constructed of the same material, for example a heat and UV stabilized nylon 12 grade for tube extrusion such as Grilamid® L25, available from EMS-Grivory. According to some embodiments the display 110 is a touch-screen display, and is able to tilt upwards and downwards by, for example, about 60 degrees each (total range of motion of 120 degrees), and pivot, or "pan" left and right by, for example, 45 degrees each (total range of motion 90 degrees) as shown by arrows 130 and 132 respectively. According to some embodiments, the cannula 102 (including the camera assembly, LED lighting and fluid ports integrated into the distal tip 120), fluid hub 104 and sliding connector 106 together form a single-use portion 140, which is designed for a single-use. According to these embodiments the single-use portion 140 is delivered to the medical practitioner in a pre-sterilized package and is intended to be disposed of after a single-use, and the handle 108 and display 110 form a re-usable portion 150, which is designed to be re-used many times.

According to some embodiments, the device 100 shown for example in FIG. 1 is a hand-held, compact single use endoscope. In these cases, endoscope 100 is provided in a sterile package, so is ready for immediate use without requiring any preparation for diagnostic or therapeutic procedures. According to some embodiments the single use device 100 needs no sophisticated connectors such that the entire endoscope is supplied in a sterile package ready for use.

Figure 2:
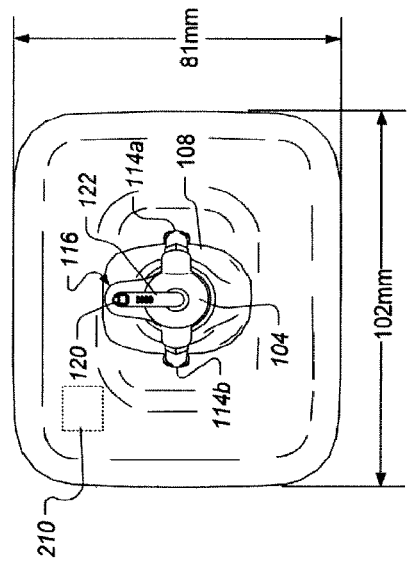
FIG. 2 is a distal end view of a self-contained, low-cost medical instrument for examining and performing operative procedures, according to some embodiments.

FIG. 2 is a distal end view of a self-contained, low-cost medical instrument for examining and performing operative procedures, according to some embodiments. The tip 120 and shaft 122 can be seen, as well as the fluid hub 104, fluid ports 114a and 114b, as well as handle body 108. Also shown, according to some embodiments is photo/video processing circuitry 210 that can be used to enhance or otherwise manipulate standard video signals and/or images received from the camera module in tip 120. According to some embodiments, in FIG. 2 as in other figures herein, various dimensions are shown that have been found to be suitable for many applications, but those skilled in the art may vary those dimensions without departing from the teachings of this patent specification.

Figure 3:
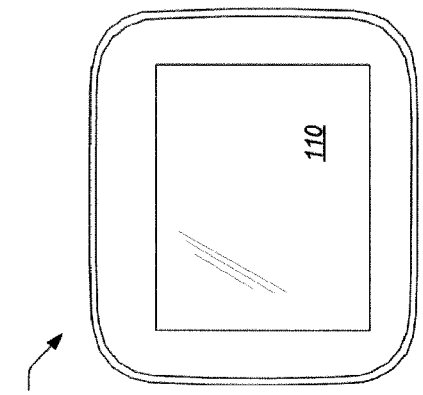
FIG. 3 is a proximal end view of a self-contained, low-cost medical instrument for examining and performing operative procedures, according to some embodiments.

FIG. 3 is a proximal end view of a self-contained, low-cost medical instrument for examining and performing operative procedures, according to some embodiments. Touch-sensitive screen 110 is preferably 3.5 inches (diagonally) In size.

Figure 4A:
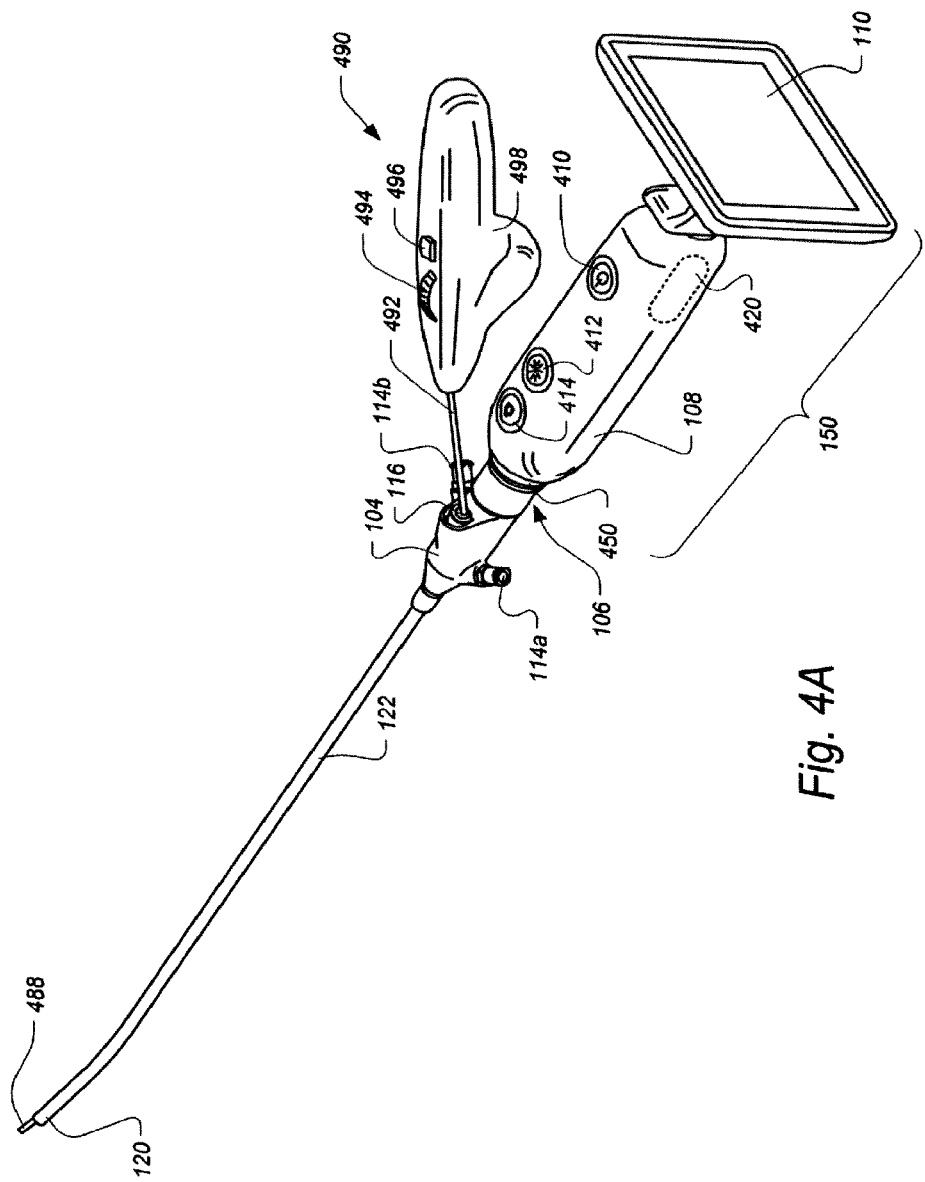
FIGS. 4A-C are perspective views of a self-contained, low-cost medical instrument for examining and performing operative procedures, according to some embodiments.
Figure 4B:
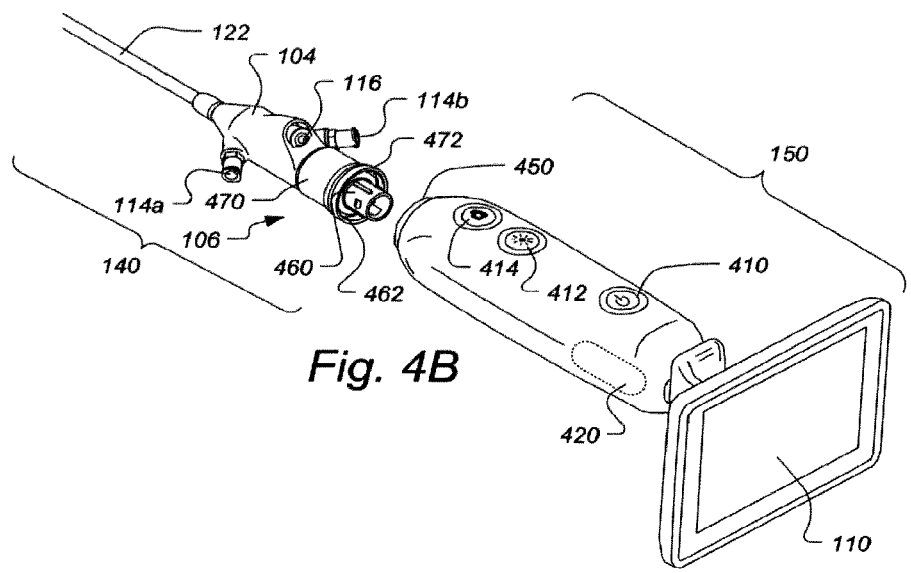
Figure 4C:
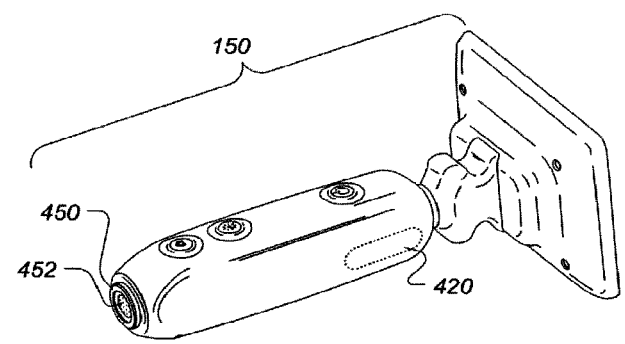

FIGS. 4A-C are perspective views of a self-contained, low-cost medical instrument for examining and performing operative procedures, according to some embodiments. In FIG. 4A the single-use portion 140 of FIG. 1 is shown attached to the re-usable portion 150, while in FIG. 4B the single-use portion 140 is shown disconnected from the re-usable portion 150. FIG. 4C shows the distal end of the re-usable portion 150. The sliding connector 106 is shown in FIG. 4B and has an outer shell 470 that includes a lip 472 that fits over an o-ring seal 462 and a protruding mating portion 450 of the handle assembly 108. Multiple similar seals can be provided along the length of connector 106 to further isolate handle 108 from patient matter and/or fluids that could otherwise contaminate and/or cause connection failure such as electrical failures on handle 108. Also within connector 106 is a seal which forms a barrier between the proximal end of an electrical cable (not shown) and fluid and/or patient matter. The electrical cable carries video signals and control signals between the camera module and LEDs at distal tip 120 to connection pins housed within sleeve 460. The sleeve 460 fits into a closed channel on the handle 108 while the connection pins mate with pin receptacles 452 as to form electrical connections with the pins.

Also visible in FIGS. 4A-C is ON/OFF button 410 which is used to toggle the device 100 on or off. According to some embodiments, the power ON/OFF button 410 is backlit using two differently colored LEDs to indicate the status of rechargeable battery 420 to the user. For example, green backlighting can be used to indicate the battery level is OK and red backlighting can be used to indicate the battery 420 is low. According to some embodiments the capacity of battery 420 is about 2500 mAh. According to some embodiments, the LED lighting of button 412 can also be used to indicate battery charging status during re-charging of the battery 420 from an external power source. In this case, the backlighting LED shows red while charging the battery and green when the battery 420 is fully charged. According to some embodiments, the ON/OFF button 410 doubles as a "home" button, such that a shorter press, such as 1 second or less, of button 410 brings up a home screen menu on the display 110.

LED brightness control button 412 is used to control the brightness of the LEDs on the distal tip 120. According to some embodiments a total of four different LED illumination levels has been found to be suitable and the single button 412 controls the level by cycling through the levels, changing the illumination level with each button press. The Snap/Video button 414 is used to capture still images and/or video from the camera in tip 120. According to some embodiments, pressing Snap/Video button 414 for three seconds or less captures a single still photo, while pressing button 414 for longer than three seconds starts video recording. When video is being recorded, a single press of button 414 stops video capture. According to some embodiments, an audible acknowledgement signal is associated with presses of the buttons 410, 412 and 414. For example, a single "beep" is sounded when any of the buttons except for double beeps when either the Snap/Video button 414 or an OK software button is pressed.

It has been found that providing dedicated hardware buttons on the handle itself have several advantages over touch-screen implemented "soft buttons" and/or hardware buttons located in locations other than the the handle. The handle located hardware buttons, such as shown in FIGS.

4A-C, allow for one-handed operation as well as for operation with gloved and/or wet hands. With one-handed operation, a user can use a single hand to both manipulation of scope and operate buttons such as the "snap" and/or the "LED" buttons. The user's other hand is then free for other procedures or for manipulating the cannula (e.g. bending of cannula and/or steering the cannula). In other examples, for some reason the user's other hand may not be sterile. Furthermore, it has been found that the use of touch-screen implemented soft buttons on touch screen display 110 may not reliably work with gloved and/or wet fingers.

Also visible in FIG. 4A is Essure® tubal sterilization delivery system 490. System 490 includes a delivery handle 498 on which thumbwheel 494 and release button 496 are mounted. The delivery catheter 492 passes through entry point 116 of device 100. The catheter passes through the operative channel of cannula 122 and distal micro insert tip 488 is shown protruding from the distal tip 120 of device 100. According to some embodiments, other types of operative devices that could be used with device 100 include: hysteroscopic scissors, biopsy forceps, grasping forceps, or other hysteroscopic instruments" directed through the operative channel. In some cases, it is desirable to use a straight distal end of cannula 122 rather than bent as shown in the case of FIG. 4A.

Figure 5:
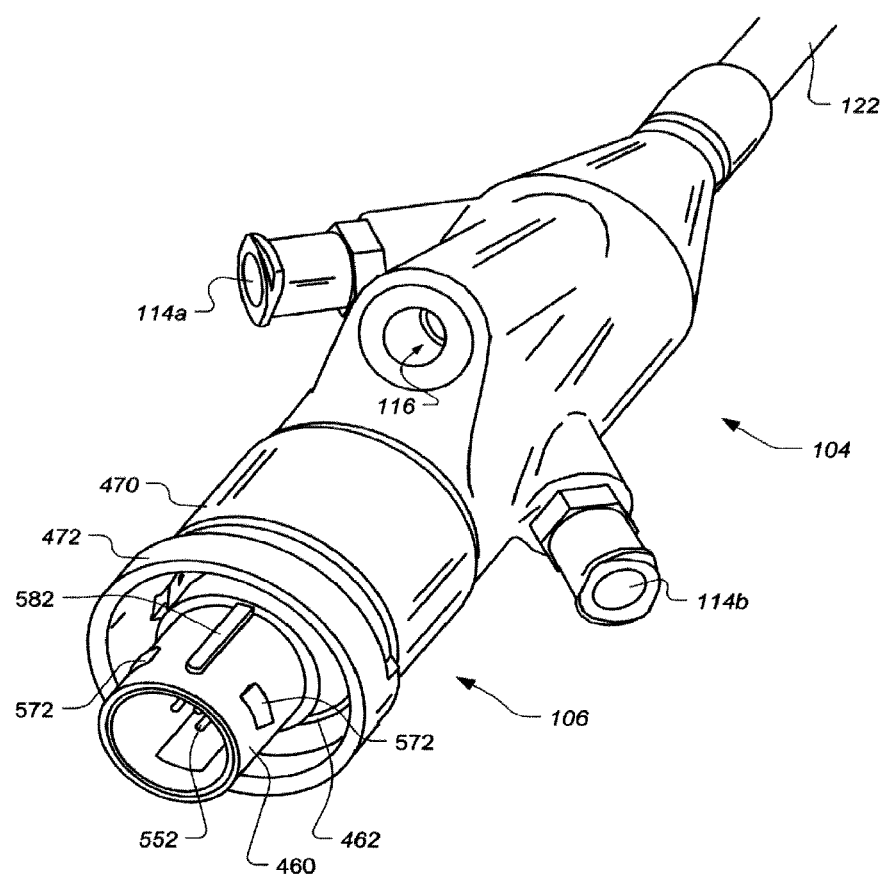
FIG. 5 is a perspective view of a fluid hub and sliding connector of a single-use portion of self-contained, low-cost medical instrument for examining and performing operative procedures, according to some embodiments.

FIG. 5 is a perspective view of a fluid hub and sliding connector of a single-use portion of self-contained, low-cost medical instrument for examining and performing operative procedures, according to some embodiments. The sliding connector 106 is shown with outer shell 470 that includes lip 472 that fits over sealing o-ring 462 a protruding portion of handle 108 (not shown). Also visible is the tip of one of the electrical connection pins 552 housed within sleeve 460. The sleeve 460 also includes three protruding bumps 572 that are shaped to fit into depressions on the handle 108 (not shown). Also visible on sleeve 460 is a longitudinally oriented tab 582 on sleeve 460 that fits into a matching channel on the handle 108 (not shown) that aids in proper rotational orientation of the single-use portion with respect to the multiple-use portion during attachment to one another. Visible on fluid hub 104 is in-flow fluid port 114a (i.e. for flowing fluid into the patient's uterus), and out-flow port 114b (i.e. for flowing fluid out of the patient's uterus). The operative device entry point 116 on hub 104 is also visible.

Figure 6:
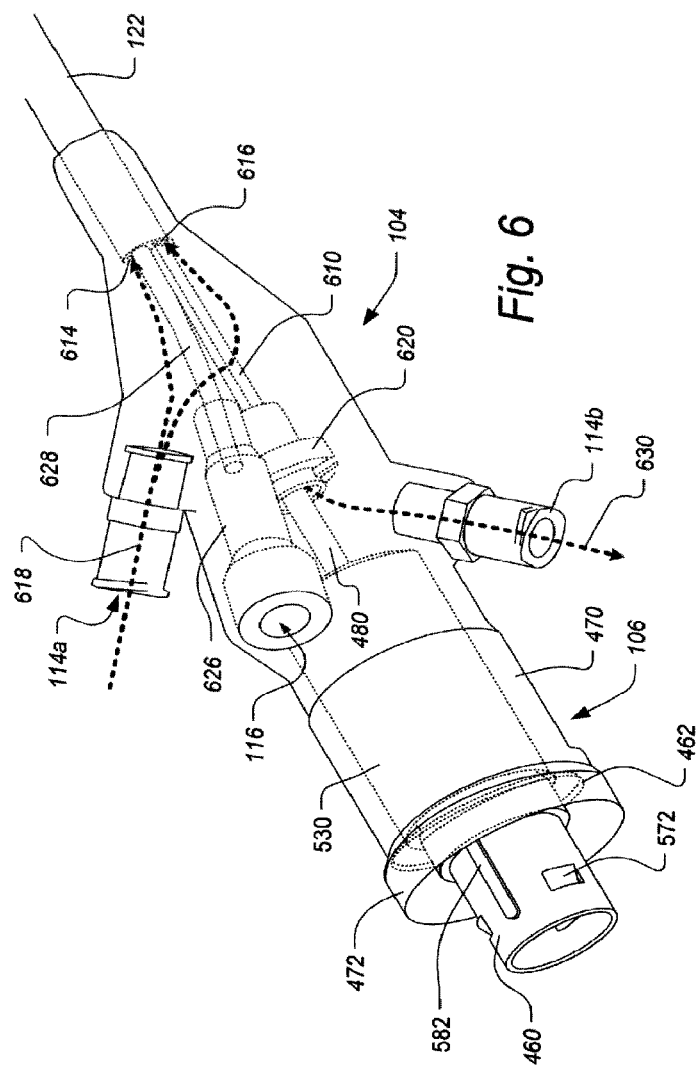
FIG. 6 is a perspective view showing some internal structures of a fluid hub and sliding connector of a single-use portion of self-contained, low-cost medical instrument for examining and performing operative procedures, according to some embodiments.

FIG. 6 is a perspective view showing some internal structures of a fluid hub and sliding connector of a single-use portion of self-contained, low-cost medical instrument for examining and performing operative procedures, according to some embodiments. Visible in FIG. 6 are further details of the fluid flow paths for fluid ports 114a and 114b. For in-flow, fluid enters fluid port 114a and travels within fluid hub 104 to enter two in-flow fluid lumens 614 and 616 within cannula 122, as shown by the dotted arrows 618. For fluid out-flow, fluid flows through a lumen within cannula 122 that is also used for electrical cable 480. The out-flow fluid and electrical cable 480 pass through steel conduit 610 which has a rectangular cross section and is dimensioned to fit securely in the lumen within cannula 122 and gasket 620. Steel conduit 610 can be sealed with cannula 122 and with gasket 620 using glue or ultrasonic bonding or a combination thereof. The out-flow fluid passes out from conduit 610 and through out-flow fluid port 114b a shown by dotted arrow 630. Electrical cable passes through barrier 530 and is in electrical communication with the connection pins (not shown) within sleeve 460.

The operative device entry point 116 is connected to operative channel tubing 628 via sleeve 626. Sleeve 626 also houses a duckbill seal (not shown) that is shaped so as to allow passage of an operative device but to inhibit fluid flow from the operative channel back out of the entry point 116. According to some embodiments operative channel tubing 628 is designed so as to decrease or prevent backflow or leaking out of the working channel entrance 116 through the use of non-wetting surface on the interior of tubing 628. The tubing 628 also should be designed so as to have a long enough length and appropriate diameter to be effective for a given maximum expected back pressure. It has been found that leakage prevention or minimization can be provided by having a small diameter, long, non-wetting surface on the inner diameter of the tubing 628. Fluid will tend to bead up on the non-wetting surface (as opposed to spreading out and drawn into a thin layer across the surface). It has been found that Fluoropolymers have a suitable non-wetting surface characteristic for a plastic material. According to some embodiments, the inner diameter of the tubing 628 can be coated with or be entirely constructed from a fluoropolymer. Common fluoropolymer suitable materials are PTFE (polytetrafluoroethylene), PFA (perfluoroalkoxy polymer), and FEP (fluorinated ethylene-propylene). They are often referred to under the trade name Teflon® (DuPont). Coatings such as Kynar® can also be used to threat the inner surface of tubing 628 to make it non wetting. According to some embodiments the inner surface of sleeve 626 can also be coated with the same or similar material so as to inhibit leakage from entry point 116.

Figure 7:
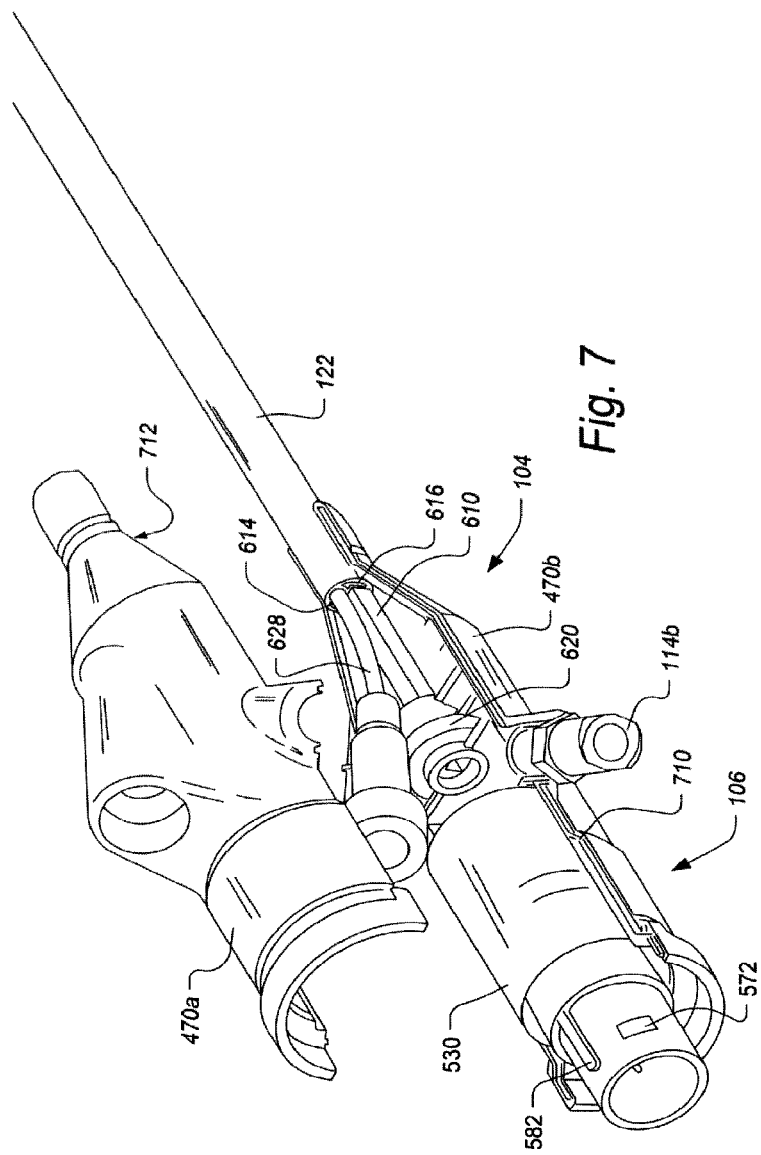
FIG. 7 is a perspective view illustrating how an outer shell can be formed of two halves for use in a low-cost medical instrument for examining and performing operative procedures, according to some embodiments.

FIG. 7 is a perspective view illustrating how an outer shell can be formed of two halves for use in a low-cost medical instrument for examining and performing operative procedures, according to some embodiments. Forming the outer shell 470 of connector 106 and hub 104 from two pre-molded halves 470a and 470b has been found that to be beneficial for both ease of manufacturing as well as enhancing the ability to form various internal seals. The two pre-molded halves 470a (upper) and 470b (lower) are bonded or welded using processes such as ultrasonic welding. A raised ridge 710 on lower shell half 470b fits in a mating channel 712 on the upper shell half 470a to further aid in ease of manufacturing and robustness of the resulting shell piece 470. Assembling the shell from two halves such as shown in FIG. 7 enhances the ability to effectively and evenly apply glue, such as glue 550 shown in FIG. 8A infra. According to some embodiments, certain interior structural components, such as barrier 530 and gasket 620, are bonded or welded ultrasonically directly to the shell 470. In such cases, the use of glue can be eliminated or at least supplemented. According to some embodiments, some or all of barrier 530 is also manufactured as two halves. During assembly the placement of the glue 554 is more easily and robustly applied to form a seal between opening 534 of barrier 530 and cable 480 (as shown in FIG. 8A, infra).

Figure 8A:
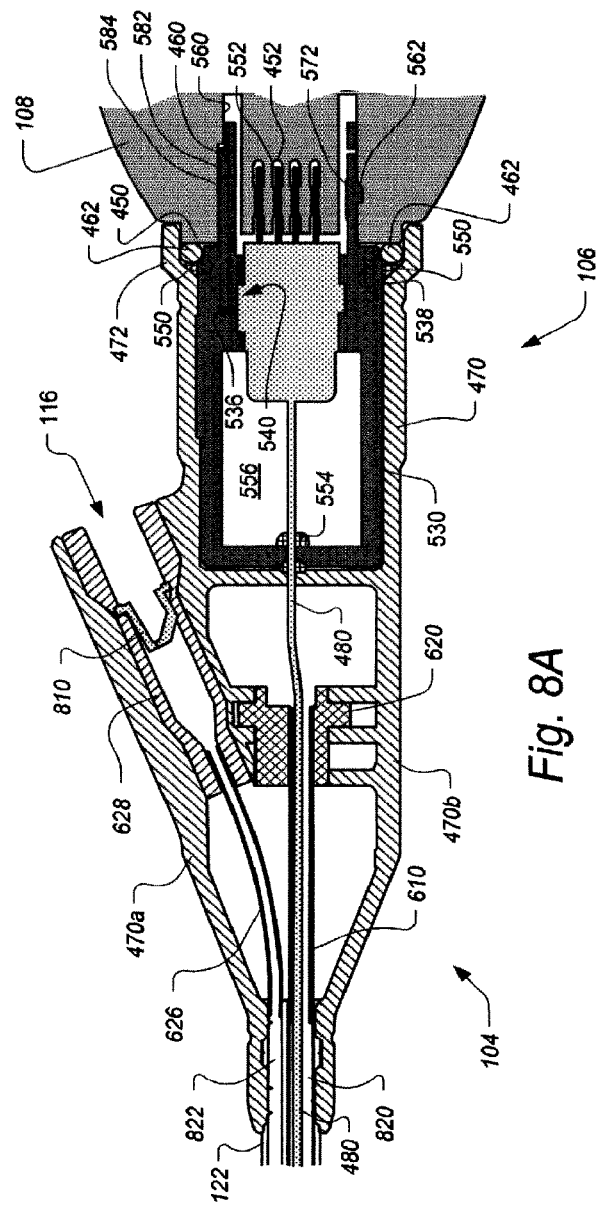
FIG. 8A is a cross section view showing further details of a sealed sliding connector and fluid hub of a self-contained, low-cost medical instrument for examining and performing operative procedures, according to some embodiments.

FIG. 8A is a cross section view showing further details of a sealed sliding connector and fluid hub of a self-contained, low-cost medical instrument for examining and performing operative procedures, according to some embodiments. The sliding connector 106 is shown here with outer shell 470 that includes lip 472 that fits over o-ring seal 462 and a protruding mating portion 450 of the handle assembly 108. Other seals can be provided along the length of connector 106 to further isolate handle 108 from patient matter and/or fluids that could otherwise contaminate and/or cause connection failure such as electrical failures on handle 108. The cable 480 carries video signals, control signals and electrical power between the camera module and LEDs at distal tip 120 to connection pins housed within sleeve 460. The sleeve 460 fits into a closed channel on the handle 108 while the connection pins 552 mate with pin receptacles 452 as to form electrical connections the pins. The sliding connector 106 includes a barrier 530 that fits tightly inside outer shell 470. According to some embodiments, transparent sealing glue 550 is applied between the barrier 530 and shell 470 as shown in FIG. 5. Barrier 530 terminates at its proximal end in an extended sleeve 460 that fits into a closed channel 560 in handle 108 such that an outwardly facing bump 572 releasably fits into an inward facing depression 562 in channel 560. Also visible is a longitudinal tab 582 on sleeve 460 that fits into longitudinal channel 584 on handle 108. Barrier 530 further includes a distal portion that terminates in a first seal 532 having an opening 534 through which cable 480 passes. An intermediate portion of barrier 530 provides an additional seal by including an inner indentation 536 tightly enveloping a radial projection 540 of the proximal portion of cable 480. Barrier 530 further includes at its proximal portion a lip 538 that helps form another additional seal by bearing against o-ring 462 to further help ensure that fluid and tissue matter will not reach interior portions of handle 108 when the instrument is in use. According to some embodiments glue 554 is used to enhance the seal between barrier 530 and cable 480 as shown. According to some other embodiments, glue 554 additionally is used to mostly or fully fill the inner void 556 of barrier 530 as well. According to some embodiments, other techniques and/or combinations of techniques are used to implement the fluid barrier between the single use portion 140 and multi-use portion 150 of the device 100. For example, the seal or seals can be implemented using structures such as gaskets, caps, o-rings alone, with each other and/or in combination with glues and/or ultrasonic welding or bonding techniques. Also visible in FIG. 8A is gasket 620 that is shaped and positioned to provide fluid communication between lumen 820 of shaft 122 and steel conduit 610 to fluid port 114b (shown in FIG. 8B, infra). Also visible within shaft 122 is operative channel 822 which is connected to tubing 626 to accept an operative device that passes through entry point 116, duck bill valve 810 and sleeve 628. As described supra, the fluid barriers and sealing shown in FIG. 8A can be implemented by one or more ultrasonic welding processes.

Figure 8B:
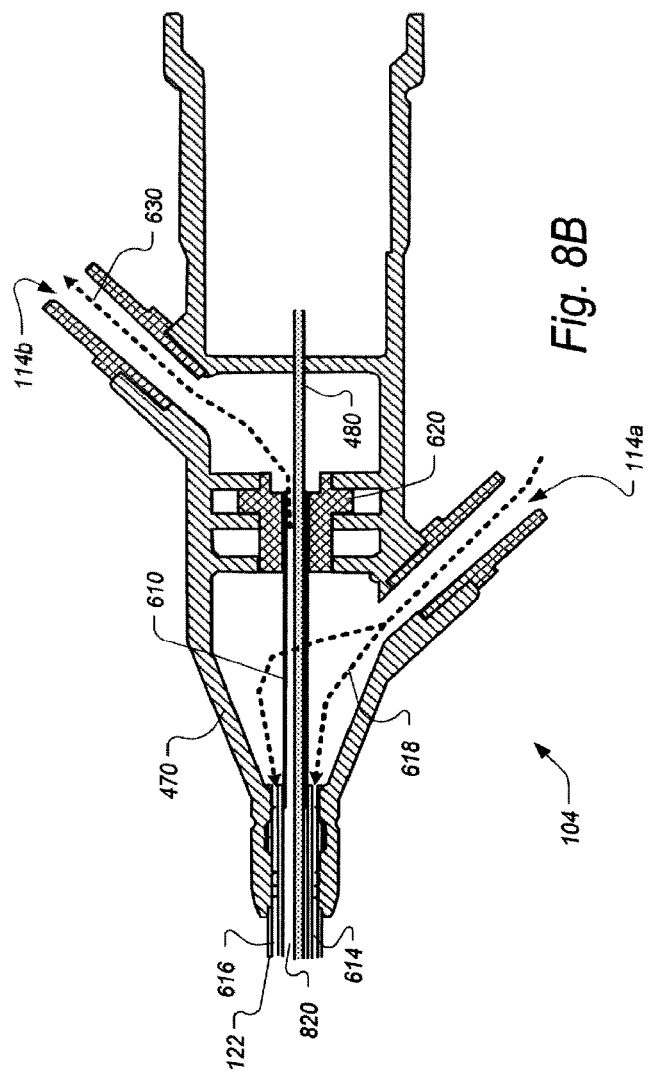
FIG. 8B is a cross section view showing further details of a fluid hub of a self-contained, low-cost medical instrument for examining and performing operative procedures, according to some embodiments.

FIG. 8B is a cross section view showing further details of a fluid hub of a self-contained, low-cost medical instrument for examining and performing operative procedures, according to some embodiments. Lumen 820 of shaft 122 is used for cable 480 and for fluid in-flow. As can be seen, steel conduit 610 and gasket 620 prevent fluid communication between lumen 820 and out-flow fluid port 114b. The fluid out-flow path is shown by dotted arrow 630. The fluid in-flow path is shown by dotted arrows 618 and as can be seen, the fluid in-flow port 114a is in direct fluid communication with in-flow lumens 614 and 618 of cannula shaft 122.

FIGS. 9A-F illustrate various aspects of a cannula for a self-contained, low-cost medical instrument for examining and performing operative procedures, according to some embodiments. FIG. 9A shows a right side view of shaft 122 of cannula 102, such as shown in device 100 of FIG. 1. The shaft 122 configured for hysteroscopic guided operative procedures using LED lighting, camera module and forward facing fluid ports on distal tip 120. The proximal end of shaft 122 includes a cutout section 920 for making fluid communication with one of the fluid lumens to a fluid port located in a fluid hub. By constructing the cannula shaft 122 from a single piece of extruded tubing, the need for additional tubes is eliminated, and it has been found that assembly yield rates are significantly improved. According to some embodiments the shaft 122 is constructed of a heat and UV stabilized nylon 12 grade for tube extrusion such as Grilamid® L25. FIG. 9B is bottom view of shaft 122 of cannula 102 showing several fluid out-flow (i.e. into the device 100) ports near the distal end. FIGS. 9A, 9B, 9D and 9E also show a cut-out region 920 near the proximal end of shaft 122. The cut-out 920 is used for fluid connection to the lumen 820 in the fluid hub according to some alternative embodiments. However, when using the stainless steel tube 610 such as shown in FIGS. 6, 7, 8A and 8B, the cut-out 920 is not used and can be eliminated.

FIG. 9C is a cross sectional view along A-A', according to some embodiments. In this case, the shaft 122 is elliptical such that it is slightly taller than it is wide. In the embodiment shown, the outer and inner walls define the operative channel 822, in-flow lumens 614 and 616, as well as the lumen 820 used for electrical cable 480 (not shown) and fluid out-flow. According to some embodiments, each of the in-flow lumens 614 and 616 have a cross sectional area of 1.65 mm$^2$. FIG. 9F is a bottom view of the distal area of shaft 122, according to some embodiments. Near the distal tip 120, a series of out-flow ports 920, 922, 924 and 926 are formed on the bottom wall of shaft 122 so as to be in fluid communication with lumen 820 of shaft 122. It has been found that providing multiple out-flow ports near the distal tip 120 is beneficial since increased flow capacity can be combined with resistance to clogging. Although four out-flow ports are shown herein, other numbers of ports can be provided, according to other embodiments.

Figure 10:
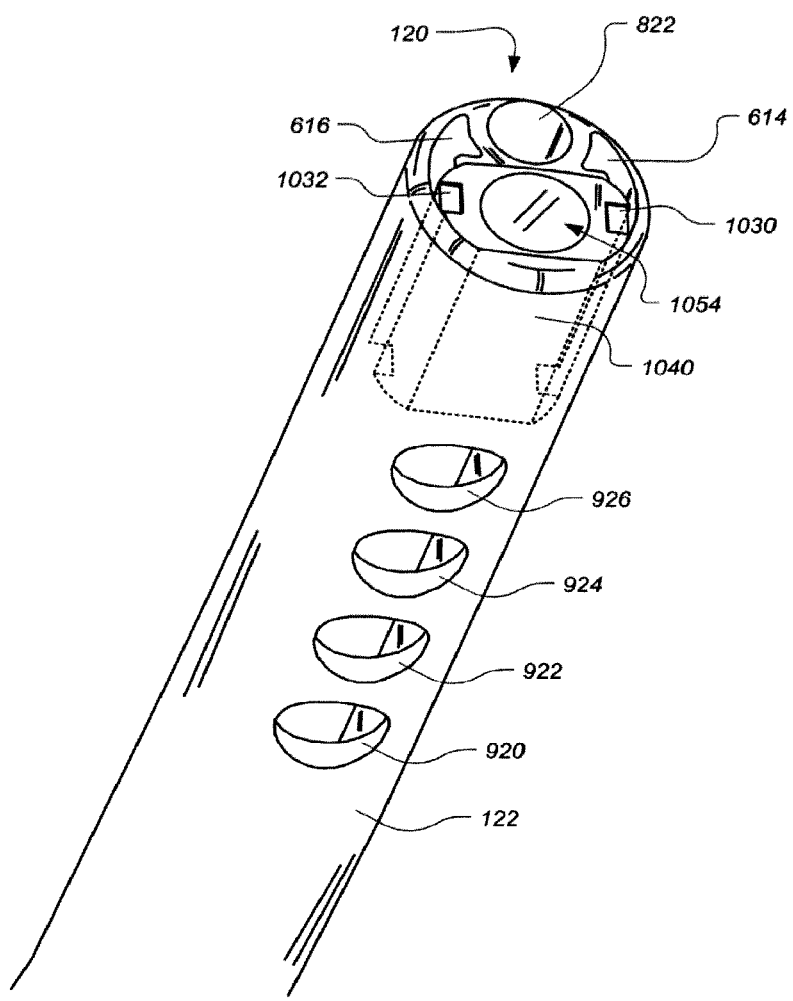
FIG. 10 is a perspective view showing further detail of a distal tip of a cannula for a self-contained, low-cost medical instrument for examining and performing operative procedures, according to some embodiments.

FIG. 10 is a perspective view showing further detail of a distal tip of a cannula for a self-contained, low-cost medical instrument for examining and performing operative procedures, according to some embodiments. The view of FIG. 10 is from the bottom as the out-flow ports 920, 922, 924 and 926 are visible on shaft 122. Also visible are the distal entrances to in-flow fluid lumens 614 and 616 as well to operative channel 822. A camera module 1054 is shown installed in the distal tip 120 of shaft 122. In particular, the camera module 1054 in primarily inserted into lumen 820. In the case shown the outer dimensions of camera module 1052 is about 3.5 mm wide, 2.4 mm tall and 5 mm deep. Since the outer dimensions of camera module 1054 are slightly larger than the lumen 820 of shaft 122, portions of the inner walls are removed to that the module 1054 can be securely glued into place as shown. Also visible on the distal tip 120 are two LEDs 1030 and 1032.

Figure 11:
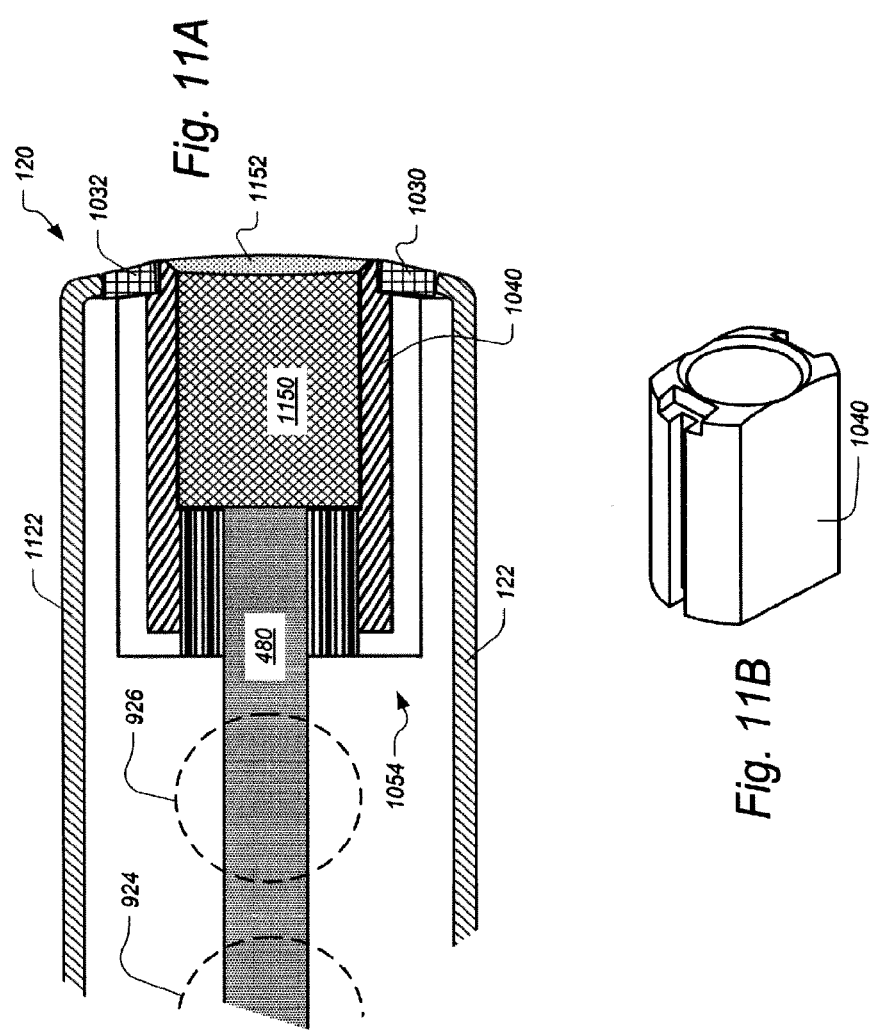
FIG. 11A is a cross section showing further detail of a distal tip of a cannula for a self-contained, low-cost medical instrument for examining and performing operative procedures, according to some embodiments.
FIG. 11B is a perspective view of a camera module holder block, according to some embodiments.

FIG. 11A is a cross section showing further detail of a distal tip of a cannula for a self-contained, low-cost medical instrument for examining and performing operative procedures, according to some embodiments. The view of FIG. 11A is from the bottom side of distal tip 120. On the distal end of the tip 120 is lens sensor stack 1150. According to some embodiments, lens sensor stack 1150 consists of a lens set (which includes an iris) precisely positioned on top of a CMOS sensor. Lens sensor stack 1150 is held together by a plastic (or in some embodiments stainless steel) housing or holder block 1040. Glass 1152 in some embodiments is simply a protective glass cover, and according to some other embodiments is the first element of the lens set. Glass 1152 is coated with hydrophobic or hydrophilic film. The lens sensor stack 1150, holder 1040 and glass 1152 together are referred to herein as camera module 1054. According to some embodiments the camera module 1054 also includes a shield (not shown) to block direct entry of light from LEDs 1030 and 1032 into the sensor lens stack 1150.

According to some embodiments, the CMOS sensor within lens sensor stack 1150 includes a low voltage color CMOS image sensor core, image sensor processing and image output interface circuitry on a single chip such as the OmniVision 7675 from OmniVision Technologies Inc. According to some other embodiments, an additional chip can be used to carry out video processing which is mounted on the same mini-PCB as the CMOS sensor. By providing integrated digital video processing within the sensor module, all video processing can be performed directly on the same PCB as the CMOS sensor, or on the same substrate in which the CMOS is formed such that the imaging plane of the CMOS and the plane along which the video processing circuits extend substantially coincide. In this example, the video signal from the sensor module can be in any suitable video format, such as NTSC, PAL, or another common video format, so that no further video processing would be required to drive widely available displays for common video formats such as TV displays, tablets, computers and hospital workstations.

The two LEDs 1030 and 1032 are positioned on either side and mounted to the camera module 1054 to evenly illuminate the uterine tissue for visual inspection. According to some embodiments each of the LEDs 1030 and 1032 are about 1.0 mm×0.5 mm in frontal area. One problem in performing visual inspections of endometrial tissues, and particularly in situations where the endometrial medium, consisting of free tissue, loosely attached tissue and/or fluid, is relatively thick, is that light reflected from tissue particles suspended close to the lens can appear overly-bright and therefore impair imaging of other tissue surfaces. As can be seen in FIG. 10, two forward facing fluid ports, 614 and 616 are provided to allow fluid to exit the tip and tend to push suspended particulate matter away from the camera so as to enhance image and video capture by camera module 1054. In some cases some tissue debris may collect on the distal surface such that imaging would be impaired in such cases the forward facing ports are useful in clearing away such collected tissue. Also it has been found that the forward facing ports are helpful in aiding insertion of the cannula in many cases as the fluid provides lubrication as well as a partial distending of tissues just ahead of the distal tip during insertion. Since the forward facing ports improve visualization, the risk of accidental damage to the uterus is greatly reduced. FIG. 11B is a perspective view of a camera module holder block 1040 which according to some embodiments is made of a suitable plastic material, such as liquid crystal polymer. The distal tip 120 in this case includes separated fluid channels for fluid in-flow and out-flow.

It has been found that it is very useful to provide the device 100 as divided into two portions: a single use portion, such a portion 140 in FIG. 1, and a re-usable portion 150 in FIG. 1. According to some embodiments, the re-usable portion includes the handle and integrated display, where some of the more costly components (such as the display) as well as some of the components that may be difficult or impractical to be re-sterilized (such as some of the electronic components) are located. According to some embodiments the separable design shown allows for different types of single-use portions to be provided that each are configured to operate with a single re-usable portion. Examples of different types of single use portions include cannulas having different port configurations (including the presence or absence of a side-facing port), different fluid hub layout configurations (including the number of fluid ports), as well cannulas having different bend locations and amount, as well as different flexibility characteristics. The selection of which cannula design to use can be a matter of preference by the user but can also be influenced by anatomical variables, as well as what type of procedure is being performed. For example, according to some embodiments, at least three main types of single-use cannula are provided that are all compatible with a re-usable handle and display portion: (1) a diagnostic cannula having in-flow capability for distention and visualization, but without a dedicated out-flow port for sampling; (2) a combined visualization and biopsy cannula which is configured for both visualization and taking tissue samples; and (3) an operative cannula that includes visualization as well as a working channel for performing one or more different types of surgical procedures (for example, single-use portion 140).

Figure 12:
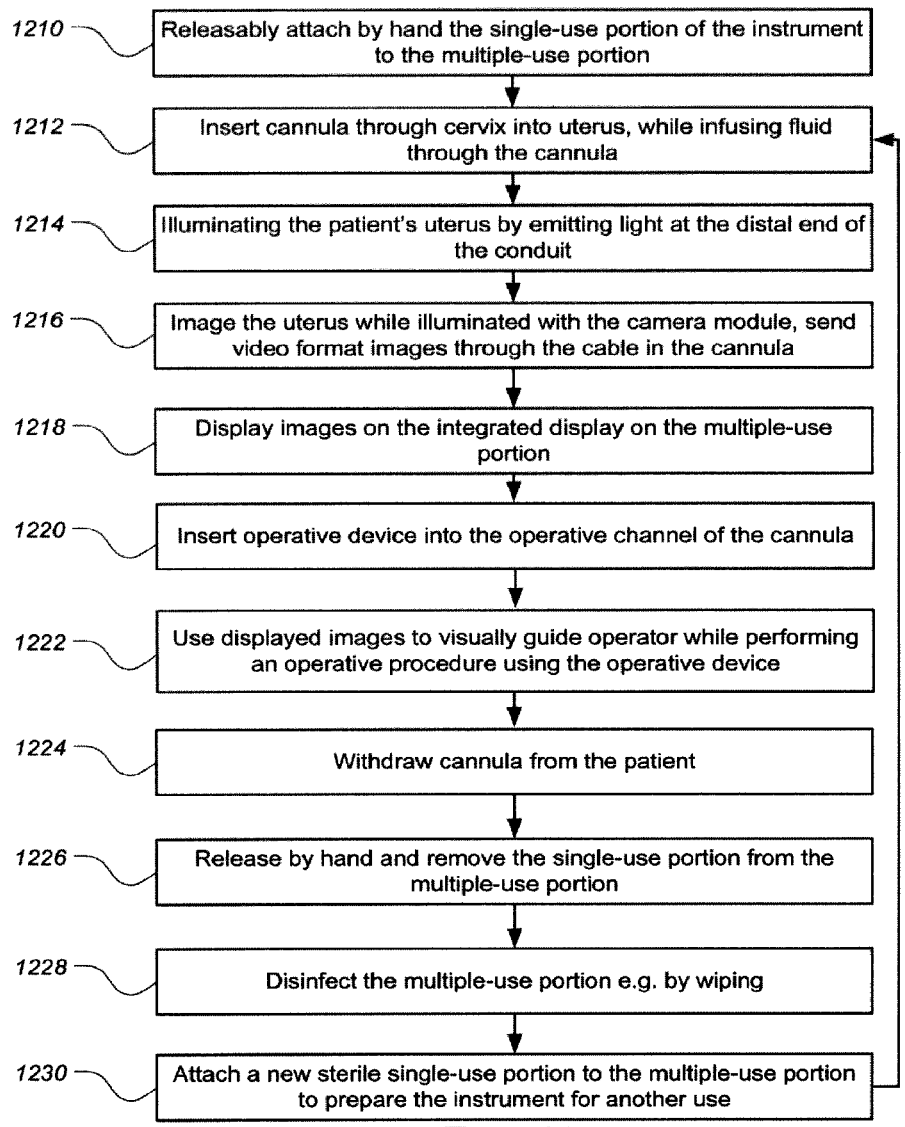
FIG. 12 is a flow chart illustrating aspects of performing an operative procedure using a self-contained, low-cost medical instrument having a single-use portion and a multiple use portion, according to some embodiments.

FIG. 12 is a flow chart showing aspects of using an operative cannula for performing an operation in a patient's uterus, according to some embodiments. In step 1210, the packaging enclosing the sterile single-use portion is opened and the single-use portion is attached to the re-usable portion. In step 1212, the distal end of the cannula is inserted into a cavity, such as through the cervix to the uterus, while infusing fluid through the cannula. In step 1214, the patient's uterus is illuminated by emitting light at the distal end of the cannula. In step 1216, the patient's uterus is imaged while illuminated with the camera module, and video format images are sent through the cable in the cannula. In step 1218, the images are displayed on the integrated display of the multiple-use portion. In step 1220, an operative device is inserted through the operative channel of the cannula. In step 1222, the displayed images are used to visually guide an operator while performing the operative procedure using the operative device. In step 1224, the cannula is withdrawn from the patient. In step 1226, the single-use portion and multiple-use portion are detached from one another by hand. The single-use portion typically is disposed of following the single use. In step 1228, the multiple-use portion of the instrument is disinfected, for example by wiping the exterior with disinfectant. Note that due to the barriers and/or seals described herein, the internal surfaces of multiple-use portion are not normally contaminated with any patient fluid or tissue and therefore will not normally be internally sterilized which is a time consuming process (and possibly damaging to some of the components of the multiple-use portion). In step 1230, a new sterile single use portion is attached to the multiple-use portion. The instrument is now ready for another use with a patient.

Figure 13:
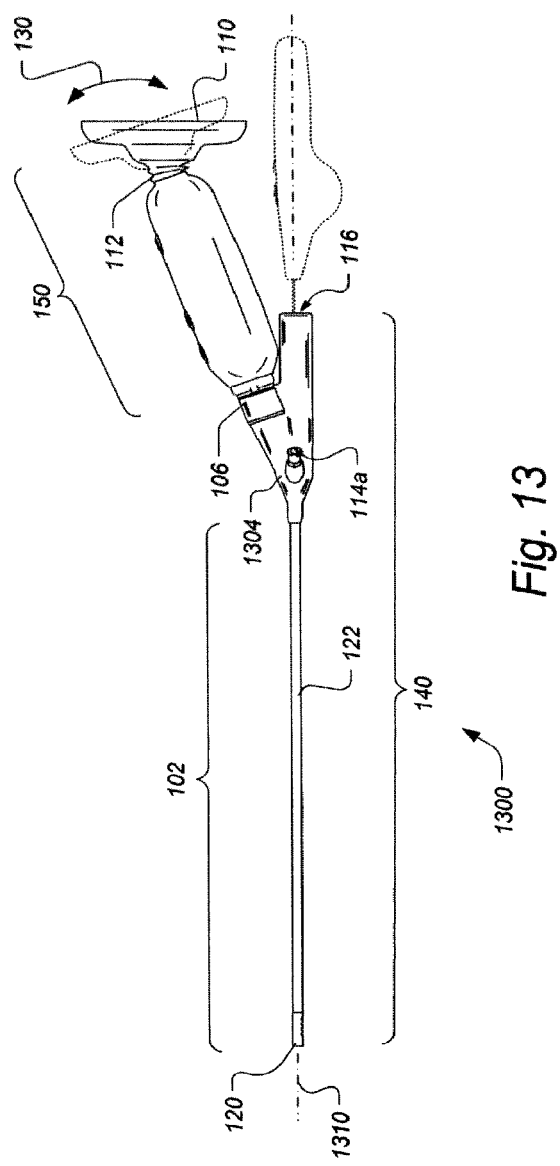
FIG. 13 illustrates a self-contained, low-cost medical instrument for examining and performing operative procedures, according to an alternative embodiment.

FIG. 13 illustrates a self-contained, low-cost medical instrument for examining and performing operative procedures, according to an alternative embodiment. Device 1300 is similar or identical to device 100 of FIG. 1 except (1) the shaft 122 is straight instead of bent near the distal tip 120, and (2) the fluid hub 1304 is arranged such that the operative device insertion point 116 is positioned in-line with the main longitudinal axis 1310 of the device. The sliding connector 106 is positioned so as to be offset from axis 1310 as shown. Note that the multi-use portion 150 of the device 1300 can be identical to the that shown in FIG. 1 which allows for cost savings for medical facilities that may want to stock different types of inexpensive single-use portions while owning only one or a small number of muliple-use portions. The in-line arrangement shown in FIG. 13 allows for straight non-bending channel through device 1300 which may be desirable for certain operative procedures.

Figure 14:
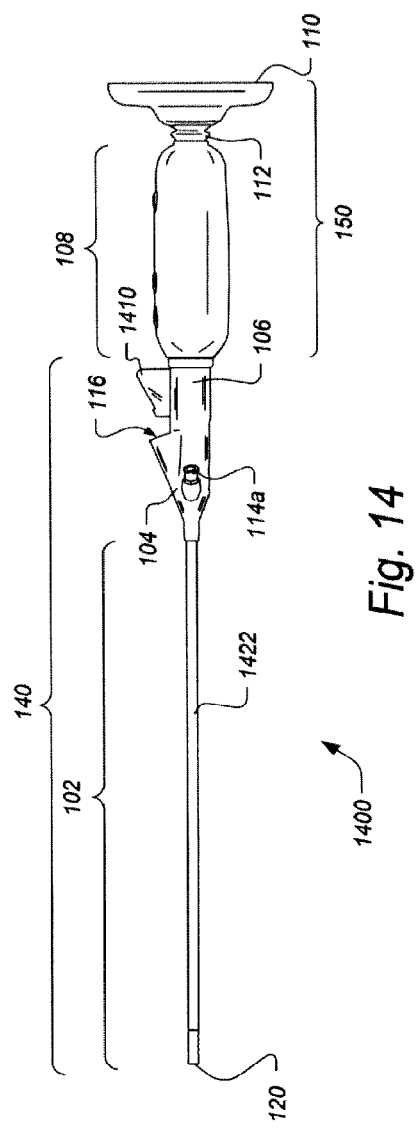
FIG. 14 illustrates a self-contained, low-cost medical instrument for endoscopically guided localized drug delivery, according to some embodiments.

FIG. 14 illustrates a self-contained, low-cost medical instrument for endoscopically guided localized drug delivery, according to some embodiments. As in the case of FIG. 13, device 1400 is similar or identical to device 100 of FIG.

1 in nearly all respects. The cannula shaft 122 is straight rather then bent near the distal tip, although in some embodiments the shaft can also be bend at various angles depending on the application. Also, a needle alignment tab 1410 is mounted on the top surface of the outer shell of fluid hub 104 and connector 106 as shown. Note that the multi-use portion 150 of the device 1300 can be identical to the that shown in FIG. 1.

Figure 15A:
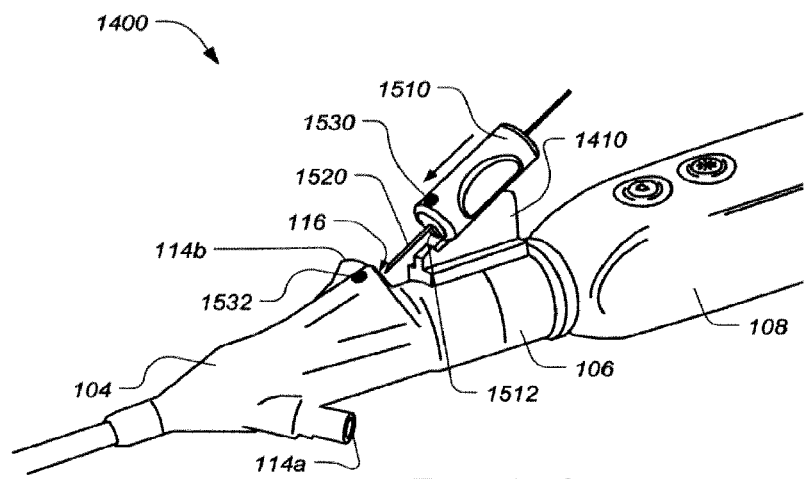
FIGS. 15A-B are perspective views illustrating aspects of a self-contained, low-cost medical instrument for endoscopically guided localized drug delivery, according to some embodiments.
Figure 15B:
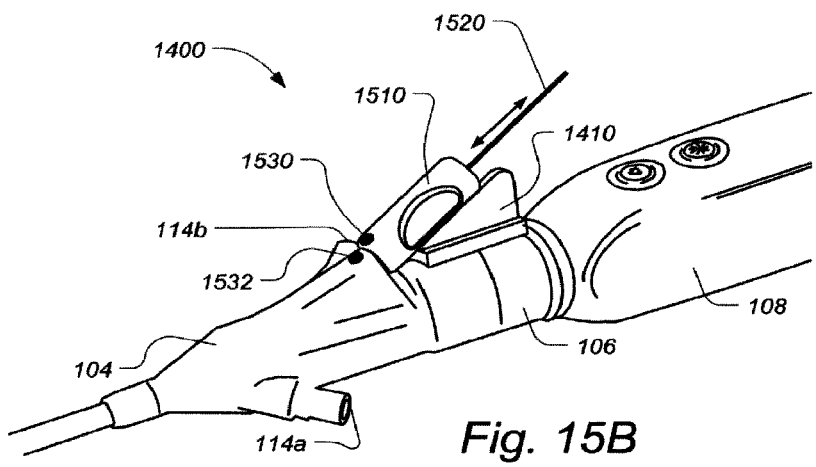

FIGS. 15A-B are perspective views illustrating aspects of a self-contained, low-cost medical instrument for endoscopically guided localized drug delivery, according to some embodiments. FIG. 15A shows a needle 1520 which is to be inserted into the operative channel of cannula 120 via insertion point 116. Note that the piercing tip 1522 has an edge (portion 1710 shown in FIG. 17, infra) that is beveled upwards so as to prevent the tip 1522 catching on any of the inner surfaces of device 1400. Two matching alignment marks 1530 and 1532 are provided on the sliding alignment lock (SAL) 1510 and fluid hub 104 respectively, so as to aid in proper orientation of the needle 1520 with respect to the device 1400. When properly aligned using marks 1530 and 1532, the SAL has a notch 1512 that accepts the alignment tab 1410 such that the needle and SAL remain in proper alignment. The SAL is slid along the alignment tab 1410 until it rests against the entry point 116 as shown in FIG. 15B.

Figure 16A:
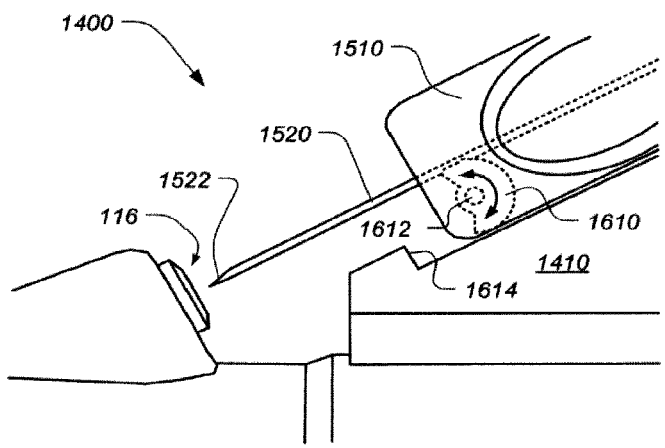
FIGS. 16A-D illustrate further aspects of a self-contained, low-cost medical instrument for endoscopically guided localized drug delivery, according to some embodiments.
Figure 16B:
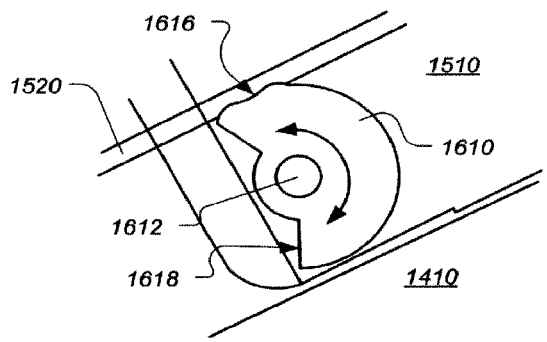
Figure 16C:
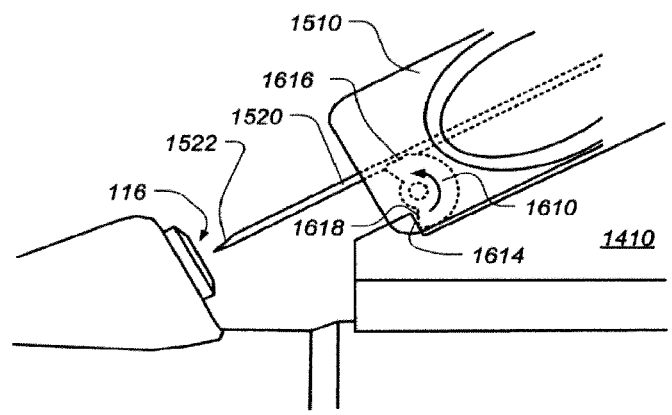
Figure 16D:
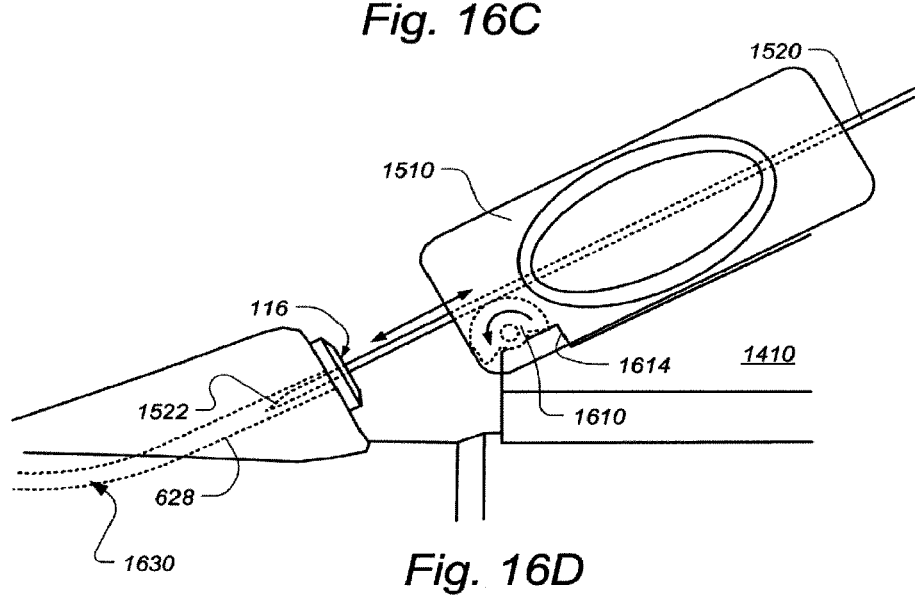
Figure 17:
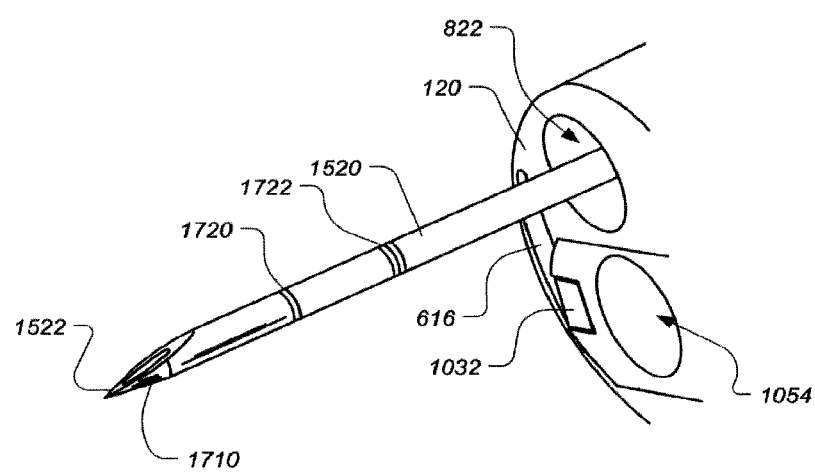
FIG. 17 is a close-up perspective view showing the beveled tip of an injection needle of an operative device, according to some embodiments.

FIGS. 16A-D illustrate further aspects of a self-contained, low-cost medical instrument for endoscopically guided localized drug delivery, according to some embodiments. In FIG. 16A is a side view showing a locking cam 1610 inside the SAL 1510 that initially locks the needle 1520 with respect to the SAL. The locking is provided by a raised locking region 1616 of cam 1610, as shown in FIG. 16B, that pushes against needle 1520 when cam 1610 is in the position shown in FIGS. 16A and 16B. The cam 1610 is shaped with a flat edge 1618 that engages against an unlocking key 1614 that protrudes from alignment tab 1410 as shown in FIGS. 16A, 16C and 16D. As the SAL is slid downward towards the entry point 116, the flat edge 1618 engages against the unlocking key 1614 as shown in FIG. 16C. The engagement acts to rotate the cam 1610 in a counter-clockwise direction about cam axis 1612 which moves the locking region 1616 of cam 1610 out of engagement with needle 1520. As shown FIG. 16D, only when the tip 1522 of needle 1520 has pass through the opening of entry point 116 is the needle unlocked by the cam 1610 within the SAL 1510. At this point the needle 1520 is free to be advanced further into tubing 628 and eventually through the operational channel 822 of shaft 122 as shown in other figures supra. According to some embodiments, the spacing of the tip 1522 of the needle 1520 with respect to SAL 1510 is such that the needle 1520 is not unlocked by the cam 1610 until the tip 1522 has passed the bent portion 1630 of tubing 628. This ensures that tip 1522 is maintained in proper alignment until after it has passed through region 1630. FIG. 17 is a close-up perspective view showing the beveled tip of needle 1510, according to some embodiments. According to some embodiments, needle 1520 has depth markings 1720 and 1722 that aid in controlling the depth of deployment of the needle 1520 under visual guidance using camera module 1054. According to some embodiments the coatings on tubing 628 and/or the use of a duck bill valve are used to inhibit back flow of fluid through entry point 116, as is described in further detail, supra.

Figure 18:
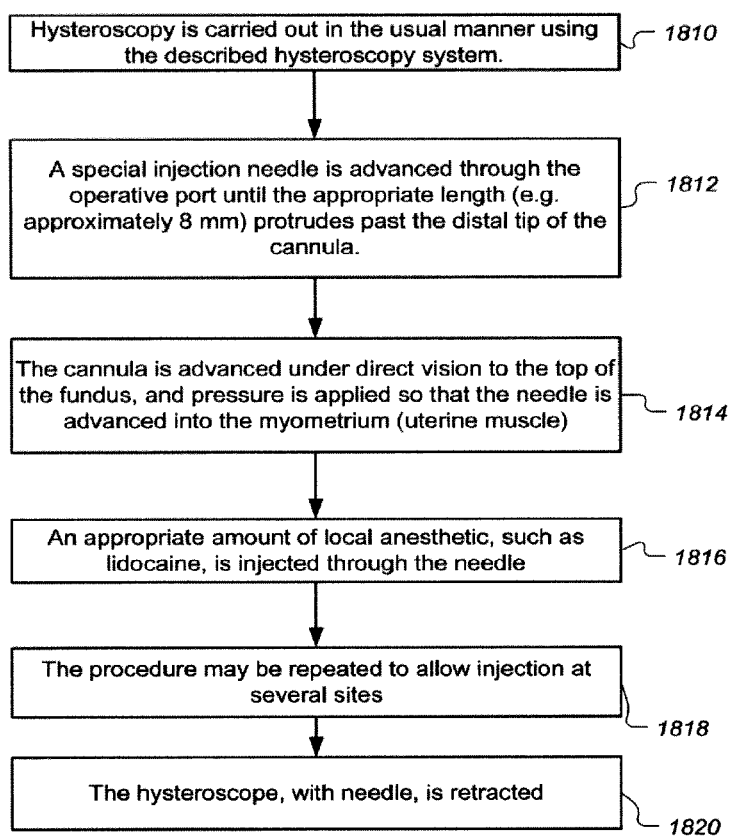
FIG. 18 is a flow chart illustrating aspects of techniques for intra cavitary anesthesia, according to some embodiments.

FIG. 18 is a flow chart illustrating aspects of techniques for intra cavitary anesthesia, according to some embodiments. In step 1810, hysteroscopy is carried out in the usual manner using the hysteroscopy system described herein. In step 1812, without withdrawing the device from the patient, a special injection needle is advanced through the operative channel of the device until the appropriate length (e.g. about 8 mm) protrudes pas the distal tip of the cannula. In step 1816, an appropriate amount of local anesthetic, such as lidocane, is injected through the needle. In step, 1818, injections can be performed at one or more other sites as desired by the operator. In step 1820, the hysteroscope with the needle are withdrawn from the patient.

Figure 19:
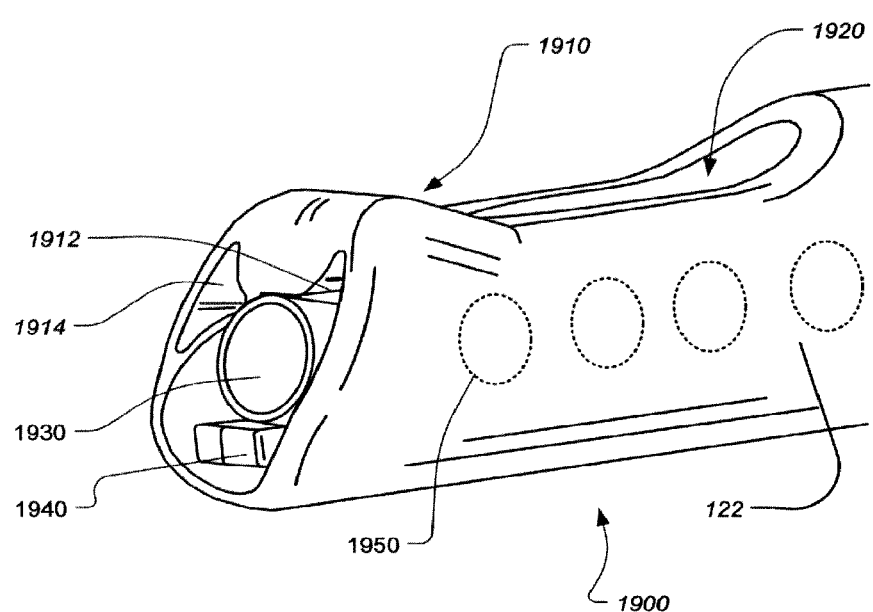
FIG. 19 is a perspective view illustrating detail of distal tip of a cannula for a self-contained, low-cost medical instrument for examining and performing operative procedures, according to an alternative embodiment.

FIG. 19 is a perspective view illustrating detail of distal tip of a cannula for a self-contained, low-cost medical instrument for examining and performing operative procedures, according to an alternative embodiment. The tip 1900 of shaft 122 can be mounted on a cannula similar or identical to that shown in FIG. 1. The tip 1900 has a ramp section 1910 near the distal end of operative channel opening 1920. The ramp shape 1910 can be desirable for certain types of operative procedures. Fluid in-flow to aid visualization, device insertion, and/or distention is through two forward facing in-flow ports 1912 and 1914. Imaging is carried out using camera module 1930 as illuminated by LEDs 1940. Outflow can take place through the operative channel opening 1920. According to one alternative embodiment, outflow takes place via multiple outflow side ports 1950 as well through port 1912. In this embodiment, the only in-flow port is the forward facing port 1914.

Figure 20:
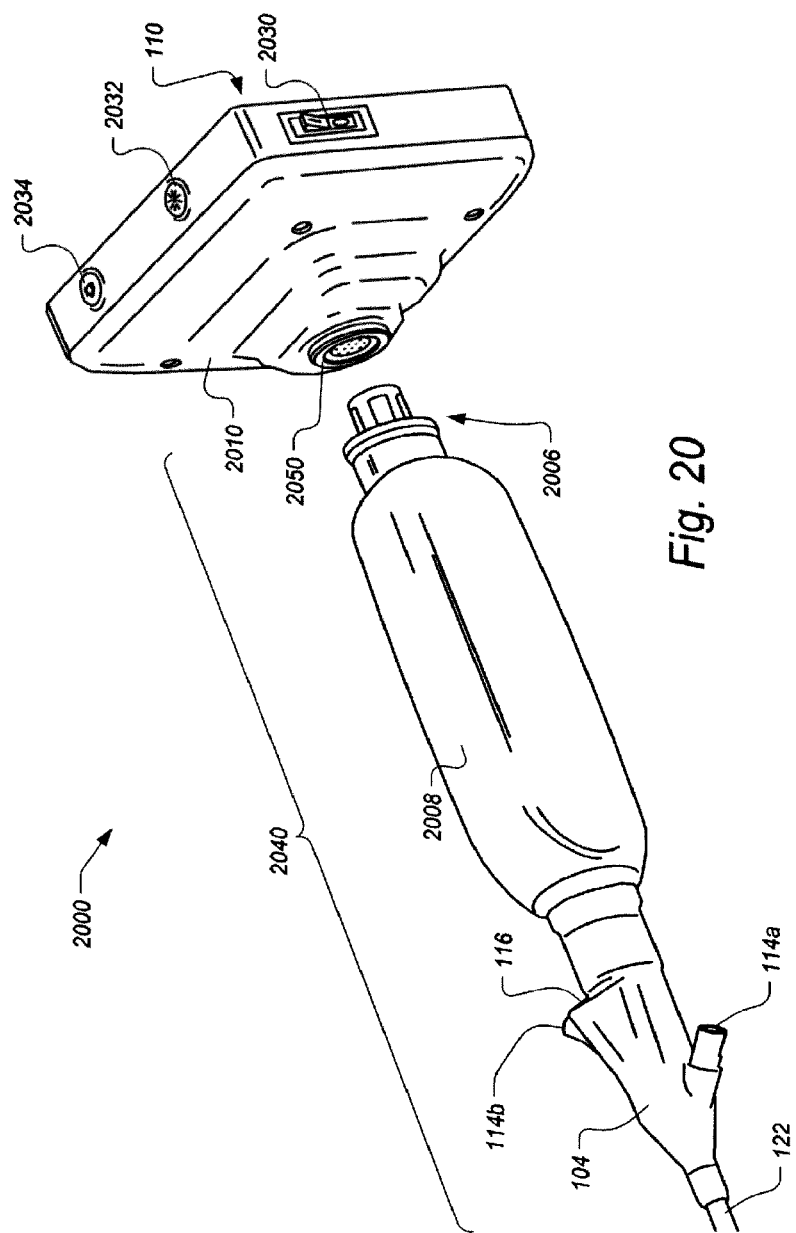
FIG. 20 illustrates a low-cost medical instrument for examining and performing operative procedures having a single use cannula, fluid hub and handle, and a re-usable display screen, according to some embodiments.

Although the junction between the single use portion 140 and the re-usable portion 150 is shown between the fluid hub and handle 108 in FIG. 1, according to some embodiments the junction can be positioned in other locations. It has been found that the most costly components of the endoscopic device are associated with the integrated display. As such, according to some embodiments, the single use portion can include the handle, while the re-usable portion includes the display. FIG. 20 illustrates low-cost medical instrument for examining and performing operative procedures having a single use cannula, fluid hub and handle, and a re-usable display screen, according to some embodiments. Device 2000 has a single use portion 2040 and a re-usable display screen in a display screen assembly 2010. The single use portion includes: a cannula that has a distal tip (not shown) and shaft 122; a fluid hub 104 that has fluid ports 114a, 114b and operative device entry point 116; a handle 2008 and a sliding connector 2006. According to some embodiments, the cannula and fluid hub 104 can be identical to those structures as described elsewhere herein. The handle 2008 can include the control buttons, electronics and battery, such as handle 108 described herein. According to some embodiments in order to reduce the cost of the single-use portion 2040, some or all of the system electronics and/or the battery can be located in the display screen assembly 2010. A sliding connector 2006 forms a connection between the display assembly 2010 and the handle 2008. The sliding connector 2006 preferably includes some or all of the fluid barriers and seals described with respect to connector 106, in order to prevent fluid from entering mating portions of the connector 2006 and/or the system electronics and LCD display 110 in display assembly 2010. According to some embodiments, one or more of on/off button 2030, LED lighting control button 2032 and "snap" button 2034 can be located on the display assembly 2010 so that the user can control the device 2000 using hardware buttons, which may be easier to use with gloved or wet hands, for example, while maintaining a low-cost single-use portion 2050. According to some other embodiments, soft-buttons can be used on touch screen 110 on display assembly 2010.

According to some alternative embodiments, one or more of the devices shown and described herein can be used for cost-effective high-quality endoscopically guided operative procedures in areas of the body other than the uterus. Examples include: cystoscopy and bladder biopsy, for diagnosis of bladder cancer and other disorders, and/or injection of medication into the bladder; ureteroscopy; endotracheal intubation and introduction of medication, such as a topical anesthetic, into the trachea; bronchoscopy and diagnosis and treatment of endobronchial disorders; thoracoscopy; laparoscopy, such as in emergency situations and remote areas. In general, the techniques described herein can be used for endoscopy of any region of the body amenable to conventional endoscopic procedures.

Although the foregoing has been described in some detail for purposes of clarity, it will be apparent that certain changes and modifications may be made without departing from the principles thereof. It should be noted that there are many alternative ways of implementing both the processes and apparatuses described herein. Accordingly, the present embodiments are to be considered as illustrative and not restrictive, and the body of work described herein is not to be limited to the details given herein, which may be modified within the scope and equivalents of the appended claims.

What is claimed is:

1. An endoscopic device, comprising:
   a single-use portion, comprising:
      an elongate conduit comprising a proximal portion and comprising a distal portion configured for insertion into a uterus of a patient, the distal portion defining a distal opening through which fluid can be delivered to the uterus,
      an imaging system disposed along the distal portion of the elongate conduit for imaging the uterus,
      an electrical cable extending from the proximal portion of the elongate conduit to the imaging system,
      a fluid hub connected to the proximal portion of the elongate conduit, the fluid hub comprising a fluid connection port and a gasket at which a first seal is provided, and
      a sliding connector attached to a proximal end of the fluid hub that isolates fluid to the single-use portion, the sliding connector comprising:
         an outer shell, and
         a fluid barrier disposed within the outer shell and surrounding the electrical cable, wherein the fluid barrier and the electrical cable together form a second seal at a distal end of the fluid barrier, and wherein the fluid barrier and the electrical cable together form a third seal located proximal to the second seal and along a radial projection of the electrical cable that seats within a radial recess of the fluid barrier; and
   a multiple-use portion configured to be attached to and detached from the single-use portion, the multiple-use portion comprising:
      a handle coupled to the proximal end of the outer shell of the sliding connector and being located proximal to the sliding connector and to the fluid hub such that the handle, the sliding connector, the fluid hub, and the elongate conduit are arranged in an in-line configuration, and
      an integral image display located proximal to the handle and electrically coupled to the imaging system by the electrical cable.

2. The endoscopic device of claim 1, wherein the elongate conduit defines a fluid channel in fluid communication with the distal opening at the distal portion of the elongate conduit and with the fluid connection port of the fluid hub, the first fluid channel being configured to deliver fluid through the distal opening to the uterus.

3. The endoscopic device of claim 2, wherein the distal opening is positioned close to the imaging system such that fluid flowing through the distal opening pushes debris away from the imaging system and thereby aids in imaging.

4. The endoscopic device of claim 2, further comprising an illumination system disposed along the distal portion of the elongate conduit and configured to illuminate the uterus at an illumination field viewed by the imaging system.

5. The endoscopic device of claim 1, wherein at least one of the first, second, and third seals is at least partially formed by one or more ultrasonic bonding processes during manufacture.

6. The endoscopic device of claim 1, wherein the outer shell is fabricated as two pieces that are bonded together using one or more ultrasonic bonding processes during manufacture.

7. The endoscopic device of claim 1, wherein the elongate conduit defines a working channel configured to allow passage of an operative device to the uterus, the working channel including an entry port formed in the fluid hub and an exit port formed along the distal portion of the elongate conduit.

8. The endoscopic device of claim 1, wherein the distal portion of the elongate conduit is bent at an angle of between about 15 degrees and about 35 degrees from a central longitudinal axis of the elongate conduit.

9. The endoscopic device of claim 1, wherein the handle includes a plurality of buttons to control a plurality of features of the endoscopic device, wherein when the single-use and multiple-use portions, the display, the handle, the elongated conduit, and the imaging system are mounted in a fixed relationship so as to rotate in alignment about a longitudinal axis defined by the elongated conduit.

10. The endoscopic device of claim 1, further comprising one or more LED devices along the distal portion of the elongate conduit.

11. The endoscopic device of claim 1, wherein the fluid hub surrounds the proximal portion of the elongate conduit.

12. The endoscopic device of claim 1, wherein the handle seats within the proximal end of the outer shell of the sliding connector.

* * * * *

UNITED STATES PATENT AND TRADEMARK OFFICE
CERTIFICATE OF CORRECTION

PATENT NO.         : 10,362,926 B2
APPLICATION NO.    : 15/453036
DATED              : July 30, 2019
INVENTOR(S)        : Xiaolong Ouyang et al.

Page 1 of 1

It is certified that error appears in the above-identified patent and that said Letters Patent is hereby corrected as shown below:

In the Specification

<u>Column 1</u>
Line 25, after "2013" insert -- . --
Line 50, delete "81/556,167" and insert -- 61/556,167 --

Signed and Sealed this
Eighth Day of October, 2019

Andrei Iancu
*Director of the United States Patent and Trademark Office*